(12) United States Patent
Rezania

(10) Patent No.: US 9,181,528 B2
(45) Date of Patent: Nov. 10, 2015

(54) DIFFERENTIATION OF PLURIPOTENT STEM CELLS

(75) Inventor: Alireza Rezania, Skillman, NJ (US)

(73) Assignee: Janssen Biotech, Inc., Horsham, PA (US)

( * ) Notice: Subject to any disclaimer, the term of this patent is extended or adjusted under 35 U.S.C. 154(b) by 84 days.

(21) Appl. No.: 13/211,972

(22) Filed: Aug. 17, 2011

(65) Prior Publication Data

US 2012/0052576 A1    Mar. 1, 2012

Related U.S. Application Data

(60) Provisional application No. 61/378,480, filed on Aug. 31, 2010.

(51) Int. Cl.
*C12N 5/00*   (2006.01)
*C12N 5/02*   (2006.01)
*C12N 5/071*  (2010.01)

(52) U.S. Cl.
CPC ........ *C12N 5/0678* (2013.01); *C12N 2501/115* (2013.01); *C12N 2501/16* (2013.01); *C12N 2501/385* (2013.01); *C12N 2501/727* (2013.01); *C12N 2506/02* (2013.01)

(58) Field of Classification Search
None
See application file for complete search history.

(56) References Cited

U.S. PATENT DOCUMENTS

| | | |
|---|---|---|
| 3,209,652 A | 10/1965 | Burgsmueller |
| 3,845,641 A | 11/1974 | Waller |
| 3,935,067 A | 1/1976 | Thayer |
| 4,499,802 A | 2/1985 | Simpson |
| 4,537,773 A | 8/1985 | Shenvi |
| 4,557,264 A | 12/1985 | Hinsch |
| 4,737,578 A | 4/1988 | Evans et al. |
| 5,215,893 A | 6/1993 | Mason et al. |
| 5,449,383 A | 9/1995 | Chatelier et al. |
| 5,525,488 A | 6/1996 | Mason et al. |
| 5,567,612 A | 10/1996 | Vacanti et al. |
| 5,665,568 A | 9/1997 | Mason et al. |
| 5,686,090 A | 11/1997 | Schilder et al. |
| 5,713,957 A | 2/1998 | Steele et al. |
| 5,716,810 A | 2/1998 | Mason et al. |
| 5,718,922 A | 2/1998 | Herrero-Vanrell |
| 5,759,830 A | 6/1998 | Vacanti et al. |
| 5,770,417 A | 6/1998 | Vacanti et al. |
| 5,780,454 A | 7/1998 | Adams et al. |
| 5,834,308 A | 11/1998 | Peck et al. |

(Continued)

FOREIGN PATENT DOCUMENTS

| | | |
|---|---|---|
| CN | 1389565 A | 7/2002 |
| CN | 1602351 A | 3/2005 |

(Continued)

OTHER PUBLICATIONS

D'Amour et al, Nat. Biotechnol., vol. 24., No. 11, 1392-1401 (2006).*

(Continued)

*Primary Examiner* — Blaine Lankford
*Assistant Examiner* — Thomas J Visone
(74) *Attorney, Agent, or Firm* — Lois A. Gianneschi

(57) ABSTRACT

The present invention provides methods to promote the differentiation of pluripotent stem cells into insulin producing cells. In particular, the present invention provides a method utilizing a CYP26A inhibitor to produce a population of pancreatic endocrine precursor cells.

22 Claims, 10 Drawing Sheets

(56) References Cited

U.S. PATENT DOCUMENTS

| | | |
|---|---|---|
| 5,843,780 A | 12/1998 | Thomson |
| 5,908,782 A | 6/1999 | Marshank et al. |
| 5,914,262 A | 6/1999 | MacMichael et al. |
| 5,942,435 A | 8/1999 | Wheeler |
| 6,001,647 A | 12/1999 | Peck et al. |
| 6,022,743 A | 2/2000 | Naughton et al. |
| 6,083,903 A | 7/2000 | Adams et al. |
| 6,087,113 A | 7/2000 | Caplan et al. |
| 6,200,806 B1 | 3/2001 | Thomson |
| 6,261,549 B1 | 7/2001 | Fernandez et al. |
| 6,281,012 B1 | 8/2001 | McIntosh et al. |
| 6,297,217 B1 | 10/2001 | Adams et al. |
| 6,306,424 B1 | 10/2001 | Vyakarnam et al. |
| 6,328,960 B1 | 12/2001 | McIntosh et al. |
| 6,331,298 B1 | 12/2001 | Ferguson et al. |
| 6,333,029 B1 | 12/2001 | Vyakarnam et al. |
| 6,365,149 B2 | 4/2002 | Vyakarnam et al. |
| 6,413,773 B1 | 7/2002 | Ptasznik et al. |
| 6,436,704 B1 | 8/2002 | Roberts et al. |
| 6,458,589 B1 | 10/2002 | Rambhatla |
| 6,458,593 B1 | 10/2002 | Musick et al. |
| 6,509,369 B2 | 1/2003 | Scott et al. |
| 6,521,427 B1 | 2/2003 | Evans |
| 6,534,084 B1 | 3/2003 | Vyakarnam et al. |
| 6,599,323 B2 | 7/2003 | Melican et al. |
| 6,617,152 B2 | 9/2003 | Bryhan et al. |
| 6,617,317 B1 | 9/2003 | Adams et al. |
| 6,626,950 B2 | 9/2003 | Brown et al. |
| 6,642,048 B2 | 11/2003 | Xu |
| 6,656,488 B2 | 12/2003 | Yi et al. |
| 6,670,127 B2 | 12/2003 | Evans |
| 6,703,017 B1 | 3/2004 | Peck et al. |
| 6,713,446 B2 | 3/2004 | Gupta |
| 6,793,945 B2 | 9/2004 | Bathurst et al. |
| 6,800,480 B1 | 10/2004 | Bodnar et al. |
| 6,815,203 B1 | 11/2004 | Bonner-Weir et al. |
| 6,958,319 B2 | 10/2005 | Gupta |
| 6,987,110 B2 | 1/2006 | Zhang et al. |
| 7,005,252 B1 | 2/2006 | Thomson et al. |
| 7,033,831 B2 | 4/2006 | Fisk et al. |
| 7,157,275 B2 | 1/2007 | Guarino et al. |
| 7,297,539 B2 | 11/2007 | Mandalam et al. |
| 7,326,572 B2 | 2/2008 | Fisk et al. |
| 7,371,576 B2 | 5/2008 | Tsang et al. |
| 7,410,798 B2 | 8/2008 | Mandalam et al. |
| 7,413,734 B2 | 8/2008 | Mistry et al. |
| 7,442,548 B2 | 10/2008 | Thomson et al. |
| 7,449,334 B2 | 11/2008 | Thomson et al. |
| 7,510,876 B2 | 3/2009 | D;Amour et al. |
| 7,534,608 B2 | 5/2009 | Martinson et al. |
| 7,569,385 B2 | 8/2009 | Haas |
| 7,585,672 B2 | 9/2009 | Odorico et al. |
| 7,704,738 B2 | 4/2010 | D'Amour et al. |
| 7,993,920 B2 | 8/2011 | Martinson et al. |
| 8,187,878 B2 | 5/2012 | Dalton et al. |
| 2002/0072117 A1 | 6/2002 | Xu et al. |
| 2003/0082155 A1 | 5/2003 | Habener et al. |
| 2003/0138948 A1 | 7/2003 | Fisk et al. |
| 2003/0180903 A1 | 9/2003 | Bryhan et al. |
| 2004/0015805 A1 | 1/2004 | Kidd |
| 2004/0058412 A1 | 3/2004 | Ho et al. |
| 2004/0062753 A1 | 4/2004 | Rezania et al. |
| 2004/0106196 A1 | 6/2004 | Fraser et al. |
| 2004/0121460 A1 | 6/2004 | Lumelsky et al. |
| 2004/0121461 A1 | 6/2004 | Honmou et al. |
| 2004/0132729 A1 | 7/2004 | Salituro et al. |
| 2004/0161419 A1 | 8/2004 | Strom et al. |
| 2004/0171623 A1 | 9/2004 | Reynolds et al. |
| 2004/0209901 A1 | 10/2004 | Adams et al. |
| 2004/0220393 A1 | 11/2004 | Ward et al. |
| 2004/0241761 A1 | 12/2004 | Sarvetnick |
| 2005/0037488 A1 | 2/2005 | Mitalipova |
| 2005/0037491 A1 | 2/2005 | Mistry et al. |
| 2005/0053588 A1 | 3/2005 | Yin et al. |
| 2005/0054093 A1 | 3/2005 | Haas |
| 2005/0054098 A1 | 3/2005 | Mistry et al. |
| 2005/0054102 A1 | 3/2005 | Wobus et al. |
| 2005/0058631 A1 | 3/2005 | Kihm et al. |
| 2005/0063961 A1 | 3/2005 | Friedlander et al. |
| 2005/0148070 A1 | 7/2005 | Thomson et al. |
| 2005/0158852 A1 | 7/2005 | Wang et al. |
| 2005/0187298 A1 | 8/2005 | Vasudevan et al. |
| 2005/0208029 A1 | 9/2005 | Umezawa et al. |
| 2005/0233446 A1 | 10/2005 | Parsons |
| 2005/0244962 A1 | 11/2005 | Thomson et al. |
| 2005/0260749 A1 | 11/2005 | Odorico et al. |
| 2005/0266554 A1 | 12/2005 | D'Amour |
| 2006/0003446 A1 | 1/2006 | Keller |
| 2006/0030042 A1 | 2/2006 | Brivanlou et al. |
| 2006/0040387 A1 | 2/2006 | Fisk |
| 2006/0148081 A1 | 7/2006 | Kelly et al. |
| 2006/0194315 A1 | 8/2006 | Condie et al. |
| 2006/0194321 A1 | 8/2006 | Colman et al. |
| 2006/0281174 A1 | 12/2006 | Xu et al. |
| 2007/0010011 A1 | 1/2007 | Parsons |
| 2007/0082397 A1 | 4/2007 | Hasson et al. |
| 2007/0154981 A1 | 7/2007 | Hori et al. |
| 2007/0155661 A1 | 7/2007 | Kim |
| 2007/0254359 A1 | 11/2007 | Rezania |
| 2007/0259421 A1 | 11/2007 | D'Amour et al. |
| 2007/0259423 A1 | 11/2007 | Odorico |
| 2007/0264713 A1 | 11/2007 | Terstegge et al. |
| 2008/0091234 A1 | 4/2008 | Kladakis et al. |
| 2008/0241107 A1 | 10/2008 | Copland, III et al. |
| 2008/0260700 A1 | 10/2008 | Accili et al. |
| 2008/0267926 A1 | 10/2008 | Martinson et al. |
| 2008/0268533 A1 | 10/2008 | Dalton et al. |
| 2008/0268534 A1 | 10/2008 | Robins et al. |
| 2009/0004152 A1 | 1/2009 | Martinson et al. |
| 2009/0093055 A1 | 4/2009 | Fisk et al. |
| 2009/0170198 A1* | 7/2009 | Rezania ................. 435/377 |
| 2009/0203141 A1 | 8/2009 | Lin et al. |
| 2009/0263896 A1 | 10/2009 | Kelly et al. |
| 2009/0269845 A1 | 10/2009 | Rezania |
| 2009/0298178 A1 | 12/2009 | D'Amour |
| 2009/0325293 A1 | 12/2009 | Davis et al. |
| 2010/0003749 A1 | 1/2010 | Uchida et al. |
| 2010/0015100 A1 | 1/2010 | Xu |
| 2010/0015711 A1 | 1/2010 | Davis et al. |
| 2010/0028307 A1 | 2/2010 | O'Neil |
| 2010/0093053 A1 | 4/2010 | Oh et al. |
| 2010/0112693 A1 | 5/2010 | Rezania et al. |
| 2010/0255580 A1 | 10/2010 | Rezania |
| 2011/0014703 A1 | 1/2011 | Xu et al. |
| 2011/0229441 A1 | 9/2011 | Benchoua et al. |
| 2012/0045830 A1 | 2/2012 | Green et al. |

FOREIGN PATENT DOCUMENTS

| | | |
|---|---|---|
| CN | 1671835 A | 9/2005 |
| CN | 1946838 A | 4/2007 |
| CN | 101092606 A | 12/2007 |
| CN | 101310012 A | 11/2008 |
| CN | 101541953 A | 9/2009 |
| CN | 101611016 A | 12/2009 |
| EP | 0363125 A2 | 4/1990 |
| EP | 348969 B1 | 5/1993 |
| EP | 0617126 B1 | 9/1994 |
| EP | 0800829 B1 | 10/1997 |
| EP | 92302 B1 | 11/2006 |
| EP | 1873237 A1 | 1/2008 |
| EP | 1391505 B1 | 1/2009 |
| GB | 2484873 B2 | 4/2014 |
| JP | 2005506074 A2 | 3/2003 |
| JP | 2006500003 A2 | 1/2006 |
| JP | 2008500809 A2 | 1/2008 |
| JP | 2009513143 A2 | 4/2009 |
| KR | 10-2008-0020098 A | 3/2008 |
| WO | 9219759 A2 | 2/1992 |
| WO | 9847892 A1 | 10/1998 |
| WO | 9920741 A1 | 4/1999 |
| WO | 0029549 A1 | 5/2000 |
| WO | 0123528 A1 | 4/2001 |
| WO | 0151616 A2 | 7/2001 |

(56) References Cited

FOREIGN PATENT DOCUMENTS

| | | |
|---|---|---|
| WO | 0181549 A3 | 11/2001 |
| WO | 0246183 A2 | 6/2002 |
| WO | 0246197 A1 | 6/2002 |
| WO | 02086107 A2 | 10/2002 |
| WO | 02092756 A2 | 11/2002 |
| WO | 03026584 A2 | 4/2003 |
| WO | 03029445 A1 | 4/2003 |
| WO | 03033697 A1 | 4/2003 |
| WO | 03042405 A2 | 5/2003 |
| WO | 0305049 A1 | 6/2003 |
| WO | 03054169 A1 | 7/2003 |
| WO | 03062405 A2 | 7/2003 |
| WO | 03095452 A1 | 11/2003 |
| WO | 03102134 A2 | 12/2003 |
| WO | 03103972 A1 | 12/2003 |
| WO | 2004011621 A2 | 2/2004 |
| WO | 2004016747 A2 | 2/2004 |
| WO | 2004044158 A2 | 5/2004 |
| WO | 2004050827 A2 | 6/2004 |
| WO | 2004055155 A2 | 7/2004 |
| WO | 2004073633 A1 | 9/2004 |
| WO | 2004087885 A2 | 10/2004 |
| WO | 2004090110 A2 | 10/2004 |
| WO | 2005001077 A2 | 1/2005 |
| WO | 2005080598 A1 | 1/2005 |
| WO | 2005014799 A1 | 2/2005 |
| WO | 2005017117 A2 | 2/2005 |
| WO | 2005058301 A1 | 6/2005 |
| WO | 2005063971 A1 | 7/2005 |
| WO | 2005065354 A2 | 7/2005 |
| WO | 2005080551 A1 | 9/2005 |
| WO | 2005086845 A2 | 9/2005 |
| WO | 2005097977 A2 | 10/2005 |
| WO | 2005097980 A2 | 10/2005 |
| WO | 2005116073 A3 | 12/2005 |
| WO | 2006016999 A1 | 2/2006 |
| WO | 2006020919 A2 | 2/2006 |
| WO | 2006026473 A1 | 3/2006 |
| WO | 2006036925 A1 | 4/2006 |
| WO | 2006080952 A2 | 8/2006 |
| WO | 2006083782 A2 | 8/2006 |
| WO | 2006094286 A2 | 9/2006 |
| WO | 2006100490 A1 | 9/2006 |
| WO | 2006108361 A1 | 10/2006 |
| WO | 2006113470 A2 | 10/2006 |
| WO | 2006114098 A2 | 11/2006 |
| WO | 2006135824 A1 | 12/2006 |
| WO | 2006137787 A1 | 12/2006 |
| WO | 2006138433 A2 | 12/2006 |
| WO | 2007002086 A2 | 1/2007 |
| WO | 2007003525 A2 | 1/2007 |
| WO | 2007012144 A1 | 2/2007 |
| WO | 2007016485 A2 | 2/2007 |
| WO | 2007027157 A1 | 3/2007 |
| WO | 2007030870 A1 | 3/2007 |
| WO | 2007047509 A1 | 4/2007 |
| WO | 2007051038 A2 | 5/2007 |
| WO | 2007069666 A1 | 6/2007 |
| WO | 2007082963 A1 | 7/2007 |
| WO | 2007103282 A1 | 9/2007 |
| WO | 2007127927 A2 | 11/2007 |
| WO | 2007139929 A2 | 12/2007 |
| WO | 2007143193 A1 | 12/2007 |
| WO | 2007149182 A2 | 12/2007 |
| WO | 2008004990 A2 | 1/2008 |
| WO | 2008013664 A1 | 1/2008 |
| WO | 2008035110 A1 | 3/2008 |
| WO | 2008036447 A2 | 3/2008 |
| WO | 2008048647 A1 | 4/2008 |
| WO | 2008048671 A1 | 4/2008 |
| WO | 2008086005 A1 | 7/2008 |
| WO | 2008094597 A1 | 8/2008 |
| WO | 2008102118 A1 | 8/2008 |
| WO | 2009012428 A1 | 1/2009 |
| WO | 2009018453 A1 | 2/2009 |
| WO | 2009027644 A2 | 3/2009 |
| WO | 2009048675 A1 | 4/2009 |
| WO | 2009061442 A1 | 5/2009 |
| WO | 2009070592 A1 | 6/2009 |
| WO | 2009096049 A1 | 8/2009 |
| WO | 2009096902 A1 | 8/2009 |
| WO | 2009101407 A2 | 8/2009 |
| WO | 2009105570 A2 | 8/2009 |
| WO | 2009131568 A1 | 10/2009 |
| WO | 2009132083 A2 | 10/2009 |
| WO | 2009154606 A1 | 12/2009 |
| WO | 2010000415 A1 | 1/2010 |
| WO | 2010002846 A1 | 1/2010 |
| WO | 2010053472 A1 | 5/2010 |
| WO | 2010057039 A2 | 5/2010 |
| WO | 2010059775 A1 | 5/2010 |
| WO | 2011011300 A2 | 1/2011 |
| WO | 2011108993 A1 | 9/2011 |
| WO | 2012019122 A2 | 2/2012 |

OTHER PUBLICATIONS

Kinkel et al, PNAS, vol. 106, No. 19, 7864-7869 (2009).*
Stoppie et al, Pharmacol. Exp. Therapeut., vol. 293, No. 1, 304-311 (2000).*
Madsen et al, Nat. Biotechnol., vol. 24, No. 12, 1481-1483 (2006).*
Abeyta, et al., Unique Gene Expression Signatures of Independently-Derived Human Embryonic Stem Cells Lines, Human Molecular Genetics, Jan. 28, 2004, pp. 601-608, vol. 13, No. 6, Oxford University Press.
Abranches, et al., Expansion of Mouse Embryonic Stem Cells on Microcarriers, Biotechnology Bioengineering, Apr. 15, 2007, pp. 1211-1221, vol. 96, No. 6, Wiley InterScience.
Ackermann, et al., Molecular Regulation of Pancreatic B-Cell Mass Development, Maintenance, and Expansion, Journal of Molecular Endocrinology, 2007, pp. 193-206, vol. 38.
Adams, J., Proteasome Inhibition in Cancer: Development of PS-341, Seminars in Oncology, 2001, pp. 613-619, vol. 28, No. 6.
Age-Related Eye Disease Study Research Group, A Randomized, Palcebo-Controlled, Clinical Trial of High-Dose Supplementation with Vitamins C and E, Beta Carotene, and Zinc for Age-Related Macular Degeneration and Vision Loss, Arch Ophthalmology, 2001, pp. 1417-1436, AREDS Report No. 8, vol. 119.
Allegrucci, et al., Differences between Human Embryonic Stem Cell Lines, Human Reproduction Update, Aug. 26, 2006, pp. 1-18, Advance Access.
Almond, et al., The Proteasome: A Novel Target for Cancer Chemotherapy, Leukemia, 2002, pp. 433-443, vol. 16.
Amit et al., Human Feeder Layers for Human Embryonic Stem Cells, Biology of Reproduction, Jan. 22, 2003, 2150-2156, 68, No. 6, Society for the Study of Reproduction, Inc.
Amit, et al., Clonally Derived Human Embryonic Stem Cell Lines Maintain Pluripotency and Proliferative Potential for Prolonged Periods of Culture, Developmental Biology, 2000, pp. 271-278, vol. 227.
Amit, et al., Feeder Layer-and Serum-Free Culture of Human Embryonic Stem Cells, Biology of Reproduction, 2004, pp. 837-845, vol. 70.
Arai, et al., Purification of Recombinant Activin A Using the Second Follistatin Domain of Follistatin-Related Gene (FLRG), Protein Expression & Purification, 2006, pp. 78-82, vol. 49.
Armstrong, et al., The Role of P13K/AKT, MAPK/ERK and NFκβ Signalling in the Maintenance of Human Embryonic Stem Cell Pluripotency and Viability Highlighted by Transcriptional Profiling and Functional Analysis, Human Molecular Genetics, 2006, pp. 1894-1913, vol. 15, No. 11.
Baetge, Production of B-Cells from Human Embryonic Stem Cells, Diabetes, Obesity, Metabolism, 2008, pp. 186-194, vol. 10, Supplement 4.
Balsam, et al., Haematopoeitic Stem Cells Adopt Mature Haeatopoietic Fates in Ischaemic Myocardium, Nature, Apr. 8, 2004, pp. 668-673, Nature Publishing Group.
Barclay, et al., The Leucocyte Antigen Facts Book, The Leucocyte Antigen Facts Book, 1997, Textbook, 2[sup] edition, Academic Press.-

(56) References Cited

OTHER PUBLICATIONS

Beltrami, et al., Adult Cardiac Stem Cells are Multipotent and Support Myocardial Regeneration, Cell, Sep. 19, 2003, pp. 763-776, vol. 114, Cell Press.

Bigdeli, et al., Adaptation of Human Embryonic Stem Cells to Feeder-Free and Matrix-Free Culture Conditions Directly on Plastic Surfaces, Journal of Biotechnology, 2008, pp. 146-153, vol. 133.

Blin, et al., A Purified Population of Multipotent Cardiovascular Progenitors Derived from Primate Pluripotent Stem Cells Engrafts in Postmyocardial Infarcted Nonhumans Primates, The Journal of Clinical Investigation, Apr. 2010, pp. 1125-1139, vol. 120, No. 4.

Blyszczuk et al., Expression of Pax4 in embryonic stem cells promotes differentiation of nestin-positive progenitor and insulin-producing cells, Proceedings of the National Academy of Sciences, Feb. 4, 2003, 998-1003, 100-3, National Academy of Sciences.

Bocian-Sobkowska, et al., Polyhormonal Aspect of the Endocrine Cells of the Human Fetal Pancreas, Histochem Cell Biol, 1999, pp. 147-153, vol. 112, Issue 2.

Bonner-Weir et al., In vitro cultivation of human islets from expanded ductal tissue, Proceedings of the National Academy of Sciences, Jul. 5, 2000, 7999-8004, 97-14, National Academy of Sciences.

Borowiak, et al., How to Make AB Cells, Current Opinion Cell Biology, 2009, pp. 727-732, vol. 21, Issue 6.

Braam, et al., Improved Genetic Manipulation of Human Embryonic Stem Cells, Nature Methods, May 2008, pp. 389-392, vol. 5, No. 5.

Brakenhoff et al., Development of a Human Interleukin-6 Receptor Antagonist, Journal of Biological Chemistry, Jan. 7, 1994, 86-93, 269-1, US.

Brambrink, et al., Sequential Expression of Pluripotency Markers During Direct Reprogramming of Mouse Somatic Cells, Cell Stem Cell, 2008, pp. 151-159, vol. 2.

Brevig, et al., The Recognition of Adsorbed and Denatured Proteins of Different Topographies by β2 Integrins and Effects on Leukocyte Adhesion and Activation, Biomaterials, 2005, pp. 3039-3053, vol. 26.

Brevini, et al., No Shortcuts to Pig Embryonic Stem Cells, Theriogenology, 2010, pp. 544-550, vol. 74.

Bross, et al., Approval Summary for Bortezomib for Injection in the Treatment of Multiple Myeloma, Clinical Cancer Research, Jun. 15, 2004, pp. 3954-3964, vol. 10.

Brown, et al., Optimal Control of Blood Glucose: The Diabetic Patient or the Machine?, Science Translation Medicine, Apr. 14, 2010, pp. 1-5, vol. 2 Issue 27.

Burkard et al, Conditional Neuronal Nitric Oxide Synthase Overexpression Impairs Myocardial Contractility, Circulation Reseach, Jan. 18, 2007, pp. e32-e44, vol. 100.

Buzzard et al., Karyotype of human ES cells during extended culture, Nature, Apr. 1, 2004, 381-382, 22-4, Nature Publishing Group.

Cai, et al., Generation of Homogeneous PDX1+Pancreatic Progenitors from Human ES Cell-derived Endoderm Cells, Journal of Molecular Cell Biology, Nov. 12, 2009, pp. 50-60, vol. 2.

Castaing, et al., Blood Glucose Normalization Upon Transplantation of Human Embryonic Pancreas into Beta-Cell-Deficient SCID Mice, Diabetologica, 2001, pp. 2066-2076, vol. 44.

Chambers, et al., Functional Expression Cloning of Nanog, a Pluripotency Sustaining Factor in Embryonic Stem Cells, Cell, May 30, 2003, pp. 643-655, vol. 113.

Chapple, et al., Unfolding Retinal Dystrophies: A Role for Molecular Chaperones?, Trends in Molecluar Medicine, 2001, pp. 414-421, vol. 7, No. 9.

Chen, et al., A Small Molecule that Directs Differentiation of Human ESCs into the Pancreatic Lineage, Nature Chemical Biology, Apr. 11, 2009, pp. 258-265, vol. 5, No. 4.

Chen, et al., Chemically Defined Conditions for Human iPSC Derivation and Culture, Nature Methods, 2011, pp. 424-429, vol. 8, Issue 5.

Chen, et al., Differentiation of Rat Marrow Mesencymal Stem Cells in Pancreatic Islet Beta-Cells, World Journal of Gastroenterology, Oct. 15, 2004, pp. 3016-3020.

Cheon et al., Secretory Leukocyte Protease Inhibitor (SLPI) Regulate the Embryonic Differentiation During Periimplantation Stage, Biology of Reproduction, 2007, 64, 77, Society for the Study of Reproduction, Inc.

Cheon, et al., Defined Feeder-Free Culture System of Human Embryonic Stem Cells, Biol Reprod, 2005, 105.046870, DOI10/1095.

Chung, et al., Human Embryonic Stem Cell Lines Generated without Embryo Destruction, Cell Stem Cell, 2008, pp. 113-117, vol. 2.

Corbeil, et al., Rat Prominin, Like its Mouse and Human Orthologues, is a Pentaspan Membrane Glycoprotein, Biochemical and Biophysical Research Communications, 2001, pp. 939-944, vol. 285, No. 4.

Crane, et al., An Embryogenic Model to Explain Cytogenetic Inconsistencies Observed in Chorionic Villus Versus Fetal Tissue, Prenatal Diagnosis, 1988, pp. 119-129, vol. 8.

Cresta, et al., Phase I Study of Bortezomib with Weekly Paclitaxel in Patients with Advanced Solid Tumours, European Journal of Cancer, 2008, pp. 1829-1834, vol. 44.

Cure, et al., Improved Metabolic Control and Quality of Life in Seven Patients with Type 1 Diabetes Following Islet After Kidney Transplantation, Cell Therapy and Islet Transplantation, Mar. 27, 2008, pp. 801-812, vol. 85, No. 6.

D'Amour et al., Efficient differentiation of human embryonic stem cells to definitive endoderm, Nature Biotechnology, Oct. 28, 2005, 1-8, :W.1038/nbt1163, Nature Publishing Group.

D'Amour et al., Production of pancreatic hormone—expressing endocrine cells from human embryonic stem cells, Nature Biotechnology, Oct. 19, 2006, 1392-1401, 24-11, Nature Publishing Group, US.

David M. Chacko, et al., Survival and Differentiation of Cultured Retinal Progenitors Transplanted in the Subretinal Space of the Rat, Biochemical and Biophysical Research Communications, 2000, pp. 842-846, vol. 268, Academic Press.

De Coppi, et al., Isolation of Amniotic Stem Cell Lines with Potential for Therapy, Nature Biotechnology, 2007, pp. 100-106, vol. 25, No. 1.

Denning, et al., Common Culture Conditions for Maintenance and Cardiomyocyte Differentiation of the Human Embryonic Stem Cell Lines, BG01 and HUES-7, Int. J. Del. Biol., 2006, pp. 27-37, vol. 50.

Donovan, et al., The End of the Beginning for Pluripotent Stem Cells, Nature, Nov. 2001, pp. 92-97, vol. 414.

Dorrell, et al., Editorial, Stem Cell Research, 2008, pp. 155-156, vol. 1.

Doyle, et al., Cell and Tissue Culture: Laboratory Procedures in Biotechnology, Cell and Tiossue Culture: Laboratory Procedures in Biotechnology, 1995, Textbook, Textbook, Wiley.

Draper, et al., Recurrent Gain of Chromosomes 17q and 12 in Cultured Human Embryonic Stem Cells, Nature Biotechnology, 2004, pp. 53-54, vol. 22, No. 1.

Draper, et al., Surface Antigens of Human Embryonic Stem Cells: Changes Upon Differentiation in Culture, Journal Anatomy, 2002, pp. 249-258, vol. 200, Anatomical Society of Great Britain and Ireland.

Dupont-Gillain, et al., Plasma-Oxidized Polystyrene: Wetting Properties and Surface Reconstruction, Langmuir, 2000, pp. 8194-8200, vol. 16.

Edlund, Pancreatic Organogenisis—Pancreatic Mechanisims and Implications for Therapy, Nature, Jul. 1, 2002, 524-532, 3, Nature Publishing Group, US.

Ellerstrom, et al., Derivation of a Xeno-Free Human Embryonic Stem Cell Line, Stem Cells, 2006, pp. 2170-2176, vol. 24.

Ellerstrom, et al., Facilitated Expansion of Human Embryonic Stem Cells by Single-Cell Enzymatic Dissociation, Stem Cells, 2007, pp. 1690-1696, vol. 25, No. 7.

Ellmers, et al., Transforming Growth Factor-B Blockade Down-Regulates the Renin-Angiotensin System and Modifies Cardiac Remodling after Myoardial Infarction, Endocrinology, Jul. 24, 2008, pp. 5828-5834, vol. 149—Issue 11, The Endocrine Society.

Enzmann, et al., Enhanced Induction of RPE Lineage Markers in Pluripootent Neural Stem Cells Engrafted into the Adult Rat Subretinal Space, Investigative Ophthamology & Visual Science, Dec. 2003, pp. 5417-5422, vol. 44, No. 12, Association for Research in Vision and Ophthalmology.

(56) References Cited

OTHER PUBLICATIONS

Eventov-Friedman, et al., Embryonic Pig Pancreatic Tissue Transplantation for the Treatment of Diabetes, PLoS Medicine, Jul. 2006, e215, pp. 1165-1177, vol. 3, Issue 7.

Ezashi, et al., Low 02 Tensions and the Prevention of Differentiation of hES Cells, Proceedings of the National Academy of Sciences of USA, Mar. 29, 2005, pp. 4783-4788, vol. 102, No. 13.

Fauza, Amniotic Fluid and Placental Stem Cells, Ballieres Best Practice and Research Clinical Obsterics and Gynaecology, 2004, pp. 877-891, vol. 18, No. 6.

Fidler et al., Selective Immunomodulation by the Antineoplastic Agent Mitoxantrone, Journal of Immunology, Jul. 15, 1986, 727-732, 137-2, American Society of Immunologists, US.

Fischer, et al., Residues in the C-Terminal Region of Activin A Determine Specificity for Follistatin and Type II Receptor Binding, Journal of Endocrinology, 2003, pp. 61-68, vol. 176, Society for Endocrinology.

Fok, et al., Shear-Controlled Single-Step Mouse Embryonic Stem Cell Expansion and Embryoid Body-Based Differentiation, Stem Cells, 2005, pp. 1333-1342, vol. 23.

Frandsen et al., Activin B mediated induction of Pdx1 in human embryonic stemcell derived embryoid bodies, Biochemical and Biophysical Research Communications, Aug. 15, 2007, 568-574, 362, Elsevier Inc.

Fung, et al., The Effect of Medical Therapy and Islet Cell Transplantation on Diabetic Nephropathy: An Interim Report, Transplantation, Jul. 15, 2007, pp. 17-22, vol. 84, No. 1.

Gadue, et al., Wnt and TGB-B Signaling are Required for the Induction of an in vitro Model of Primitive Streak Formation Using Embryonic Stem Cells, Proceedings of the National Academy of Sciences, Nov. 7, 2006, 16806-16811, 103-45, National Academy of Sciences, US.

Gaspar, et al., Inhibition of Transforming Growth Factor Signaling Reduces Pancreatic Adenocarcinoma Growth and Invasiveness, Molecular Pharmacology, 2007, pp. 152-161, vol. 72, Issue 1.

Gershengorn et al., Epithelial-to-Mesenchymal Transition Generates Proliferative Human Islet Precursor Cells, Science, Dec. 24, 2004, 2261-2264, 306, US.

Giltaire, et al., The CYP26 Inhibitor R115866 Potentiates the Effects of All-Trans Retinoic Acid on Cultured Human Epidermal Keratinocytes, British Journal of Dermatology, 2009, pp. 505-513, vol. 160.

Ginis, et al., Differences Between Human and Mouse Embryonic Stem Cells, Developmental Biology, 2004, pp. 360-380, vol. 269.

Gosden, et al., Amniotic Fluid Cell Types and Culture, British Medical Bulletin, 1983, pp. 348-354, vol. 39, No. 4.

Graham, et al., Characteristics of a Human Cell Line Transformed by DNA from Human Adenovirus Type 5, Journal General Virology, 1977, pp. 59-72, vol. 36.

Guo, et al., Stem Cells to Pancreatic B-Cells: New Sources for Diabetes Cell Therapy, Endocrine Reviews, May 2009, pp. 214-227, vol. 30, No. 3, The Endocrine Society.

Hadley, et al., Extracellular Matrix Regulates Sertoli Cell Differentiation, Testicular Cord Formation, and Germ Cell Development In Vitro, The Journal of Cell Biology, Oct. 1985, 1511-1522, 101, Rockefeller University Press.

Hamann, et al., Phenotypic and Functional Separation of Memory and and Effector Human CD8+ T Cells, Journal of Experimental Medicine, Mar. 11, 1997, 1407-1418, 186-9, Rockefeller University Press, US.

Harb, et al., The Rho-Rock-Myosin Signaling Axis Determines Cell-Cell Integrity of Self-Renewing Pluripotent Stem Cells, Plos One, 2008, Article e3001, XP002530386, vol. 3, Issue 8.

Haruta, et al., In Vitro and In Vivo Characterization of Pigment Epithelieal Cells Differentiated from Primate Embryonic Stem Cells, Investigative Ophthalmology & Visual Science, Mar. 2004, pp. 1020-1025, vol. 45, No. 3, Association for Research in Vision and Ophthalmology.

Hasegawa, et al., A Method for the Selection of Human Embryonic Stem Cell Sublines with High Replating Efficiency After Single-Cell Dissociation, Stem Cells, 2006, pp. 2649-2660, vol. 24.

Hashemi, et al., A Placebo Controlled, Dose-Ranging, Safety Study of Allogenic Mesenchymal Stem Cells Injected by Endomyocardial Delivery after an Acute Myocardial Infarction, European Heart Journal, Dec. 11, 2007, pp. 251-259, vol. 29.

Held, et al., The Effect of Oxygen Tension on Colony Formation and Cell Proliferation of Amniotic Fluid Cells In-Vitro, Prenatal Diagnosis, 1984, pp. 171-180, vol. 4, No. 3.

Henderson, et al., Preimplantation Human Embryos and Embryonic Stem Cells Show Comparable Expression of Stage-Specific Embryonic Antigens, Stem Cells, 2002, pp. 329-337, vol. 20.

Heng, et al., Mechanical dissociation of human embryonic stem cell colonies by manual scraping after collagenase treatment is much more detrimental to cellular viability than is trypsinization with gentle pipetting, Biotechnol. Appl. Biochem., 2007, 33-37, 47, Portland Press Ltd., GB.

Herzenberg, et al., Fluorescence-activated Cell Sorting, Scientific American, 1976, 108-117, 234, Scientific American, US.

Hess, et al., Bone Marrow-Derived Stem Cells Initiate Pancreatic Regeneration, Nature Biotechnology, Jul. 2003, pp. 763-770, vol. 21, No. 7.

Hichem Frigui, et al., A Robust Competitive Clustering Algorithm With Applications in Computer Vision, IEEE, May 1, 1999, 450-465, 21-5, IEEE, US.

Ho, et al., Animal Cell Bioreactors, Animal Cell Bioreactors, 1991, 1-512, Hardcover, Butterworth-Heinemann.

Hoehn, et al., Morphological and Biochemical Heterogeneity of Amniotic Fluid Cells in Culture, Methods in Cell Biology, 1982, pp. 11-34, vol. 26, Academic Press, Inc.

Hori, et al, Growth inhibitors promote differentiation of insulin-producing tissue from embryonic stem cells, Proceedings of the National Academy of Sciences, Dec. 10, 2002, 16105-16110, 99-25, National Academy of Sciences.

Hussain, et al., Stem-Cell Therapy for Diabetes Mellitus, Lancet, 2004, pp. 203-205, vol. 364.

Ianus, et al., In Vivo Derivation of Glucose-Competent Pancreatic Endocrine Cells from Bone Marrow Without Evidence of Cell Fusion, The Journal of Clinical Investigation, Mar. 2003, pp. 843-850, vol. 111, No. 6.

Inami, et al., Differentiation of Induced Pluripotent Stem Cells to Thymic Epithelial Cells by Phenotype, Immunology and Cell Biology, Jun. 24, 2010, pp. 1-8, doi:10.1038/icb2010.96.

Int' Anker, et al., Amniotic Fluid as a Novel Source of Mesenchymal Stem Cells for Therapeutic Transplantation, Blood, Aug. 15, 2003, pp. 1548-1549, vol. 102, No. 4.

Inzunza, et al., Derivation of Human Embryonic Stem Cell Lines in Serum Replacement Medium Using Postnatal Human Fibroblasts as Feeder Cells, Stem Cells, 2005, 544-549, 23, AlphaMed Press.

Jafary, et al., Differential effect of activin on mouse embryonic stem cell differentiation in insulin-secreting cells under nestin-positive selection and spontaneous differentiation protocols, Cell Biology International, 2008, 278-286, 32, Elsevier.

Jeon, et al., Endocrine Cell Clustering During Human Pancreas Development, J Histochem Cytochem, 2009, pp. 811-824, vol. 57, Issue 9.

Jiang, et al., Generation of Insulin-Producing Islet-Like Clusters from Human Embryonic Stem Cells, Stem Cells, 2007, pp. 1940-1953, vol. 25, Issue 8.

Johansson, et al., Temporal Control of Neurogenin3 Activity in Pancreas Progenitors Reveals Competence Windows for the Generation of Different Endocrine Cell Types, Developmental Cell, Mar. 2007, pp. 457-465, vol. 12.

Kahan, Pancreatic Precursors and Differentiated Islet Cell Types from Murine Embryonic Stem Cells, Diabetes, Aug. 2003, pp. 2016-2042, vol. 52.

Kelly, et al., Cell-Surface Markers for the Isolation of Pancreatic Cell Types Derived from Human Embryonic Stem Cells, Nature Biotechnology, 2011, pp. 750-756, vol. 29, Issue 8.

Kicic, et al., Differentiation of Marrow Stromal Cells into Photoreceptors in the Rat Eye, The Journal of Neuroscience, Aug. 27, 2003, pp. 7742-7749, vol. 23, Issue 21.

(56) References Cited

OTHER PUBLICATIONS

Kingsley, The TGF-B Superfamily: New Members, New Receptors, and New Genetic Tests of Function in Different Organisms, Genes & Development, 1994, pp. 133-146, XP009011502, vol. 8, Cold Spring Harbor Laboratory Press.

Kinkel, et al., Cyp26 Enzymes Function in Endoderm to Regulate Pancreatic Field Size, Pnas, May 12, 2009, pp. 7864-7869, vol. 106, No. 19.

Kleinman et al., Basement Membrane Complexes with Biological Activity, Biochemistry, 1986, 312-318, 25, American Chemical Society.

Klimanskaya, et al., Human Embryonic Stem Cells Derived without Feeder Cells, Lancet, May 2005, pp. 1636-1641, vol. 365, No. 9471.

Koblas, et al., Differentiation of CD133-Positive Pancreatic Cells Into Insulin-Producing Islet-Like Cell Clusters, Transplantation Proceedings, 2008, pp. 415-418, vol. 40.

Kohen, et al., Characterization of Matrigel Interfaces During Defined Human Embryonic Stem Cell Culture, Biointerphases, Dec. 2009, pp. 6979.

Koller, et al., Effects of Synergistic Cytokine Combinations, Low Oxygen, and Irradiated Stroma on the Expansion of Human Cord Blood Progenitors, Blood, Jul. 15, 1992, pp. 403-411, vol. 80, No. 2.

Koyangi et al., Inhibition of the Rho/ROCK Pathway Reduces Apoptosis During Transplantatation of Embryonic Stem Cell-Derived Neural Precursors, Journal of Neurosciene Research, Sep. 7, 2007, 270-280, 86, Wiley-Liss, Inc.

Krapcho et al., Synthesis and Antineoplastic Evaluations of 5,8-Bis[(aminoalkyl)amino]-1-azaanthracene-9,10-diones, Journal of Medical Chemistry, 1985, 1124-1126, 28, American Chemical Society.

Krawetz, et al., Human Embryonic Stem Cells: Caught Between a ROCK Inhibitor and a Hard Place, BioEssays: News and Reviews in Molecular Cellular and Developmental Biology, 2009, pp. 336-343, vol. 31.

Kron, et al., Expression of Human Activin C Protein in Insect Larvae Infected with a Recombinant Baculovirus, Journal of Virological Methods, 1998, pp. 9-14, vol. 72.

Kroon, et al., Pancreatic Endoderm Derived from Human Embryonic Stem Cells Generates Glucose-Responsive Insulin-Secreting Cells in vivo, Nature Biotechnology, Apr. 2008, pp. 443-452, vol. 26, No. 4.

Ku et al., Committing Embryonic Stem Cells to Early Endocrine Pancreas In Vitro, Stem Cells, 2004, 1205-1217, 22, AlphaMed Press.

Kubo et al., Development of definitive endoderm from embryonic stem cells in culture, Development, 2004, 1651-1662, 131, The Company of Biologists.

Lanza, et al., Characteristics and Characterization of Human Pluripotent Stem Cells, Stem Cell Anthology, 2010, pp. 141, 142, 144 and 146, 1st Edition.

Laplante, et al., RhoA/ROCK and Cdc42 Regulate Cell-Cell Contact and N-Cadherin Protein Level During Neurodetermination of P19 Embryonal Stem Cells, Journal of Neurobiology, 2004, pp. 289-307, vol. 60, No. 3.

Larsen, et al., Evaluation of B-Cell Mass and Function in the Gottingen Minipig, Diabetes, Obesity and Metabolism, 2007, pp. 170-179, vol. 9, Supplement 2, Blackwell Publishing Ltd.

Lavon et al., The Effect of Overexpression of Pdx1 and Foxa2 on the Differentiation of Human Embryonic Stem Cells into Pancreatic Cells, Stem Cells, 2006, 1923-1930, 24, Alpha Med Press, IL.

Le Blanc, et al., Mesenchymal Stem Cells Inhibit and Stimulate Mixed Lymphocyte Cultures and Mitogenic Responses Independently of the Major Histocompatibility Complex, Scandinavian Journal of Immunology, 2003, pp. 11-20, vol. 57, Blackwell Publishing Ltd.

Lee et al., Establishment and Maintenance of Human Embryonic Stem Cell Lines on Human Feeder Cells Derived from Uterine Endometrium under Serum-Free Condition, Biology of Reproduction, Aug. 18, 2004, 42-49, 72.

Lee, et al., Human B-cell Precursors Mature into Functional Insulin-Producing Cells in an Immunoisolation Device: Implications for Diabetes Cell Thereapies, Transplantation, Apr. 15, 2009, pp. 983-991, vol. 87, No. 7.

Lee, et al., Retionic Acid-Induced Human Secretin Gene Expression in Neuronal Cells is Mediated by Cyclin-Dependent Kinase 1, Annals of the New York Academy of Sciences, 2006, pp. 393-398, vol. 1070.

Levenstein et al., Basic Fibroblast Growth Factor Support of Human Embryonic Stem Cell Self-Renewal, Stem Cells, Nov. 10, 2005, 568-574, 24, AlphaMed Press.

Li, et al., Generation of Rat and Human Induced Pluripotent Stem Cells by Combining Genetic Reprogramming and Chemical Inhibitors, Cell Stem Cell, Jan. 9, 2009, pp. 16-19, vol. 4.

Lilja et al., Cyclin-dependent Kinase 5 Promotes Insulin Exocytosis, Journal of Biological Chemistry, Jul. 6, 2001, 34199-34205, 36-7, JBC Papers in Press.

Lim, et al, Proteome Analysis of Conditioned Medium from Mouse Embryonic Fibroblast Feeder Layers which Support the Growth of Human Embryonic Stem Cells, Proteomics, 2002, pp. 1187-1203, vol. 2.

Liu, et al., A Novel Chemical-Defined Medium with bFGF and N2B27 Supplements Supports Undifferentiated Growth in Human Embryonic Stem Cells, Biochemical and Biophysical Research Communications, 2006, pp. 131-139, vol. 346.

Loh, et al., Genomic Approaches to Deconstruct Puripotency, Annu Rev Genomics Hum Genet, 2011, pp. 165-185, vol. 12.

Ludwig, et al., Derivation of Human Embryonic Stem Cells in Defined Conditions, Nature Biotechnology, Feb. 2006, pp. 185-187, vol. 24 No. 2.

Lumelsky, et al., Differentiation of Embryonic Stem Cells to Insulin-Secreting Structures Similar to Pancreatic Islets, Science, 2001, 1389-1394, 292, HighWire Press.

Lund, et al., Cell Transplantation as a Treatment for Retinal Disease, Progress in Retinal and Eye Research, 2001, pp. 415-449, vol. 20, No. 4, Elsevier Science Ltd.

Lund, et al., Retinal Transplantation: Progress and Problems in Clinical Application, Journal of Leukocyte Biology, Aug. 2003, pp. 151-160, vol. 74.

Lyttle, et al., Transcription Factor Expression in the Developing Human Fetal Endocrine Pancreas, Diabetologica, 2008, pp. 1169-1180, vol. 51, Spring-Verlag.

Macfarlane, et al., Glucose Stimulates Translocation of the Homeodomain Transcription Factor PDX1 from the Cytoplasm to the Nucleus in Pancreatic B-Cells, The Journal of Biological Chemistry, 1999, pp. 1011-1016, vol. 274, No. 2.

Maherali, et al., Directly Reprogrammed Fibroblasts Show Global Epigenetic Remodeling and Widespread Tissue Contribution, Cell Stem Cell, Jul. 2007, pp. 55-70, vol. 1, Elsevier, Inc.

Marshall, et al., Early Micro-and Macro-Angiopathy in the Streptozotocin, Research in Experimental Medicine, 1980, pp. 145-158, vol. 177, Springer-Verlag.

Marshall, et al., Isolation and Maintenance of Primate Embryonic Stem Cells, Methods in Molecular Biology, 2001, pp. 11-18, vol. 158.

Martin, et al, Bioreactors for Tissue Mass Culture: Design, Characterization, and Recent Advances, Biomaterials, Jul. 14, 2005, pp. 7481-7503, vol. 26.

Marzo, et al., Pancreatic Islets from Cyclin-Dependent Kinase 4/R24C (Cdk4) Knockin Mice have Significantly Increased Beta Cell Mass and are Physiologically Functional, Indicating that Cdk4 is a Potential Target for Pancreatic . . . , Diabetologia, 2004, pp. 686-694, vol. 47.

McKiernan, et al., Directed Differentiation of Mouse Embryonic Stem Cells into Pancreatic-Like or Neuronal-and Glial-Like Phenotypes, Tissue Engineering, 2007, pp. 2419-2430, vol. 13, No. 10.

McLean et al., Activin A Efficiently Specifies Definitive Endoderm from Human Embryonic Stem Cells Only When Phosphatidylinositol 3-Kinase Signaling is Suppressed, Stem Cells, 2007, 29-38, 25, AlphaMed Press.

McLin, et al., Repression of WNT/(szligbeta)-6atenin Signaling in the Anterior Endoderm is Essential for Liver and Pancreas Development, Development, 2007, pp. 2207-2217, vol. 134, Issue 12.

(56) References Cited

OTHER PUBLICATIONS

Meijer, et al., Pharmacological Inhibitors of Glycogen Synthase Kinase 3, Trends in Pharmacological Sciences, Sep. 2004, pp. 471-480, vol. 25, No. 9.
Micallef et al., Retinoic Acid Induces Pdx1-Positive Endoderm in Differentiating Mouse Embryonic Stem Cells, Diabetes, Feb. 2005, 301-305, 54, American Diabetes Association.
Michael J. Borowitz, et al., Prognostic Significance of Fluorescence Intensity of Surface Marker . . . , Blood, Jun. 1, 1997, 3960-3966, 89-11, American Society of Hematology, Washington, D.C., US.
Miller, et al., The Pig as a Model for Human Nutrition, Annual Review of Nutrition, 1987, pp. 361-382, vol. 7, Annual Reviews Inc.
Milunsky, et al., Genetic Disorders and the Fetus: Diagnosis Prevention and Treatment, Pediatric and Developmental Pathology, 2011, pp. 84, vol. 14, Society for Pediatric Pathology.
Mitalipova, et al., Preserving the Genetic Integrity of Human Embyonic Stem Cells, Nature Biotechnology, 2005, pp. 19-20, vol. 23, No. 1.
Mitsui, et al., The Homeoprotein Nanog is Required for Maintenance of Pluripotency in Mouse Epiblast and ES Cells, Cell, May 30, 2003, pp. 631-642, vol. 113, Cell Press.
Miyamoto et al., Human Placenta Feeder Layers Support Undifferentiated Growth of Primate Embryonic Stem Cells, Stem Cells, 2004, 433-440, 22, AlphaMed Press.
Miyazaki et al., Regulated Expression of pdx-1 Promotes In Vitro Differentiation of Insulin-Producing Cells From Embryonic Stem Cells, Diabetes, Apr. 2004, 1030-1037, 53, American Diabetes Association.
Moore, et al., The Corneal Epithelial Stem Cell, DNA and Cell Biology, 2002, pp. 443-451, vol. 21, No. 5/6.
Moran, et al., Bidirectional-Barbed Sutured Knotless Running Anastomosis v Classic van Velthoven in a Model System, Journal of Endourology, 2007, pp. 1175-1177, vol. 21, No. 10.
Morrison, et al., Culture in Reduced Levels of Oxygen Promotes Clonogenic Sympathoadrenal Differentiation by Isolated Neural Crest Stem Cells, Journal of Neuroscience, Oct. 1, 2000, pp. 7370-7376, vol. 20, No. 19.
Movassat, et al., Keratinocyte Growth Factor and Beta-Cell Differentiation in Human Fetal Pancreatic Endocrine Precursor Cells, Diabetologia, 2003, pp. 822-829, vol. 46.
Muchamuel, et al., Preclinical Pharmacology and in Vitro Characterization of PR-047, An Oral Inhibitor of the 20s Proteasome, Blood, Nov. 16, 2008, p. 1257, vol. 112, No. 11.
Munoz, et al., Conventional Pluripotency Markers are Unspecific for Bovine Embryonic-Derived Cell-Lines, Theriogenology, 2008, pp. 1159-1164, vol. 69.
Murtha, et al., Evaluation of a Novel Technique for Wound Closure Using a Barbed Suture, Cosmetic, Aug. 2, 2005, pp. 1769-1780, vol. 117, No. 6.
Nakagawa, et al., Generation of Induced Pluripotent Stem Cells without Myc from Mouse and Human Fibroblasts, Jan. 2008, pp. 101-106, vol. 26, No. 1.
Nakamura, et al., Ocular Surface Reconstruction Using Cultivated Mucosal Epithelial Stem Cells, Cornea, Oct. 2003, S75-S80, vol. 22, Supplement 1.
Nicholas et al., A Method for Single-Cell Sorting and Expansion of Genetically modified Human Embryonic Stem Cells, Stem Cells and Development, 2007, 109-117, 16, Mary Ann Liebert, Inc.
Nishimura, et al., Expression of MafA in Pancreatic Progenitors is Detrimental for Pancreatic Development, Developmental Biology, 2009, pp. 108-120, vol. 333.
Nostro, et al., Stage-Specific Signaling Through TGF Family Members and WNT Regulates Patterning and Pancreatic Specification of Human Pluripotent Stem Cells, Development, 2011, pp. 861-871, vol. 138, Issue 5.
Oh, et al., Human Embryonic Stem Cells: Technological Challenges Towards Therapy, Clinical and Experimental Pharmacology and Physiology, 2006, pp. 489-495, vol. 33.
Okita, et al., Generation of Germline-Competent Induced Pluripotent Stem Cells, Nature, Jul. 19, 2007, pp. 313-317, vol. 448.
Orlowski, et al., Safety and Antitumor Efficacy of the Proteasome Inhibitor Carfilzomib (PR-171) Dosed for Five Consecutive Days in Hematologic Malignancies: Phase 1 Results, Blood, 2007, Part 1, vol. 110, No. 11.
Osborne, et al., Some Current Ideas on the Pathogenesis and the Role of Neuroprotection in Glaucomatous Optic Neuropathy, European Journal of Ophthalmology, 2003, S19-S26, vol. 13, Supplement 3, Wichtig Editore.
Ostrom, et al., Retinoic Acid Promotes the Generation of Pancreatic Endocrine Progenitor Cells and Their Further Differentiation into B-Cells, PLOS One, Jul. 30, 2008, e2841, pp. 1-7, vol. 3, No. 7.
Paling, et al., Regulation of Embryonic Stem Cell, Self-Renewal by Phosphoinositide 3-kinase-dependent Signaling, Journal of Biological Chemistry, 2004, pp. 48063-48070, vol. 279, No. 46.
Panchision, et al., Optimized Flow Cytometric Analysis of Central Nervous System Tissue Reveals Novel Functional Relationships Among Cells Expressing CD133, CD15, and CD24, Stem Cells, 2007, pp. 1560-1570, vol. 25.
Panepinto, et al., The Yucatan Miniature Pig: Characterization and Utilization in Biomedical Research, Laboratory Animal Science, Aug. 1986, pp. 344-347, vol. 36, No. 4, American Association for Laboratory Animal Science.
Pangas, et al., Production and Purification of Recombinant Human Inhibin and Activin, Journal of Endocrinology, 2002, pp. 199-210, vol. 172.
Pardo, et al., Coming CellBIND Surface: An Improved Surface for Enhanced Cell Attachment, Corning Technical Report, 2005, 8 page report, XP002530385.
Paris, et al., Equine Embryos and Embryonic Stem Cells: Defining Reliable Markers of Pluripotency, Theriogeneology, 2010, pp. 516-524, vol. 74.
Peerani, et al., Niche-Mediated Control of Human Embryonic Stem Cell Self-Renewal and Differentiation, The EMBO Journal, 2007, pp. 4744-4755, vol. 26.
Peter O. Krutzik, et al., Coordinate Analysis of Murine Immune Cell Surface Markers and Intracellular Phosphoproteins by Flow Cytometry, Journal of Immunology, May 30, 2005, 2357-2365, 175, American Association of Immunologists, Inc., US.
Phillips, et al., Attachment and Growth of Human Embryonic Stem Cells on Microcarriers, Journal of Biotechnology, 2008, pp. 24-32, vol. 138.
Pouton, et al., Embryonic Stem Cells as a Source of Models for Drug Discovery, Nature Reviews Drug Discovery, Aug. 2007, pp. 1474-1776, vol. 6, No. 8.
Prichard, et al., Adult Adipose Derived Stem Cell Attachment to Biomaterials, Biomaterials, 2006, pp. 936-946, vol. 28, No. 6.
Prowse, et al., A Proteome Analysis of Conditioned Media from Human Neonatal Fibroblasts Used in the Maintenance of Human Embryonic Stem Cells, Proteomics, 2005, pp. 978-989, vol. 5.
Prusa, et al., Oct-4-Expressing Cells in Human Amniotic Fluid: a New Source for Stem Cell Research?, Human Reproduction, 2003, pp. 1489-1493, vol. 18, No. 7.
Rajagopal, et al, Insulin Staining of ES Cell Progeny from Insulin Uptake, Science, Jan. 17, 2003, pp. 363, vol. 299.
Rao, Conserved and Divergent Paths that Regulate Self-Renewal in Mouse and Human Embryonic Stem Cells, Developmental Biology, Aug. 10, 2004, pp. 269-286, vol. 275, Elsevier, Inc.
Rebbapragada, et al., Myostatin Signals Through a Transforming Growth Factor B-Like Signaling Pathway to Block Adipogenesis, Molecular and Cellular Biology, 2003, pp. 7230-7242, vol. 23, No. 20.
Rebollar, et al, Proliferation of Aligned Mammalian Cells on Laser-Nanostructured Polystyrene, Biomaterials, 2008, pp. 1796-1806, vol. 29.
Reisner, Growing Organs for Transplantation form Embryonic Precursor Tissues, Immunol. Res., 2007, pp. 261-273, vol. 38.
Reubinoff et al., Embryonic stem cell lines from human blastocysts: somatic differentiation in vitro, Nature Biotech, Apr. 18, 2000, 399-404, 18, Nature America Inc.
Rezania, Production of Functional Glucagon-Secreting-Cells from Human Embryonic Stem Cells, Diabetes, 2011, pp. 239-247, vol. 60, Issue 1.

(56) References Cited

OTHER PUBLICATIONS

Richards et al., Comparative Evaluation of Various Human Feeders for Prolonged Undifferentiated Growth of Human Embryonic Stem Cells, Stem Cells, 2003, 546-556, 21, AlphaMed Publlishing.

Richardson, et al., Bortezomid (PS-341): A Novel, First-in-Class Proteasome Inhibitor for the Treatement of Multiple Myeloma and Other Cancers, Cancer Control, 2003, pp. 361-369, vol. 10, No. 5.

Ricordi et al., Automated Method for Isolation of Human Pancreatic Islets, Diabetes, Apr. 1988, 413-420, 37, American Diabetes Association.

Ryan, et al., Clinical Outcomes and Insulin Secretion After Islet Transplantation with the Edmonton Protocol, Diabetes, Apr. 2001, pp. 710-719, vol. 50.

Sakaguchi, et al., Integration of Adultmesenchymal Stem Cells in the CNS, Society for Neuroscience Abstract Viewer and Itineray Planner, 2002, XP002519394, Program 237.18.

Sato et al., Maintenance of Pluripotency in Human and Mouse Embryonic Stem Cells Through Activation of Wnt Signaling by a Pharmacological GSK-3-specific Inhibitor, Nature Medicine, Jan. 2004, pp. 55-63, vol. 10, No. 1.

Sato, et al., Manipulation of Self-Renewal in Human Embryonic Stem Cells Through a Novel Pharmacological GSK-3 Inhibitor, Methods in Molecular Biology, 2006, pp. 115-128, vol. 331.

Sato, et al., Molecular Signature of Human Embryonic Stem Cells and its Comparison with the Mouse, Developmental Biology, Apr. 23, 2003, pp. 404-413, vol. 260.

Savino et al., Generation of Interleukin-6 Receptor Antagonists by Molecular-Modeling Guided Mutagenesis of Residues Important for gp130 Activation, EMBO Journal, 1994, 1357-1367, 13-6, IT.

Schraermeyer, et al., Subretinally Transplanted Embryonic Stem Cells Rescue Photoreceptor Cells From Degeneration in the RCS Rats, Cell Transplantation, 2001, pp. 673-680, vol. 10.

Schroeder, et al., Differentiation of Mouse Embryonic Stem Cells to Insulin-Producing Cells, Nature Protocols, 2005, pp. 495-507, vol. 1, No. 2.

Scullica, et al., Diagnosis and Classification of Macular Degenerations: an Approach Based on Retinal Function Testing, Documenta Ophthalmologica, 2001, pp. 237-250, vol. 102.

Seaberg et al., Clonal identification of multipotent precursors from adult ~ mouse pancreas that generate neural and pancreatic lineages, Nature Biotechnology, Sep. 2004, 1115-1124, 22, Nature Publishing Group.

Segev, et al., Differentiation of Human Embryonic Stem Cells into Insulin-Producing Clusters, Stem Cells, Jan. 1, 2004, pp. 265-274.

Shackleton, et al., Generation of a Functional Mammary Gland from a Single Stem Cell, Nature, Jan. 1, 2006, pp. 84-88, XP002567665, vol. 439.

Shamblott et al., Derivation of pluripotent stem cells from cultured human primordial germ cells, Developmental Biology, Nov. 1998, 13726-13731, 95, National Academy of Sciences.

Shapiro, et al., Islet Transplantation in Seven Patients with Type 1 Diabetes Mellitus Using a Glucocorticoid-Free Immunosuppressive Regimen, The New England Journal of Medicine, Jul. 27, 2000, pp. 230-238, vol. 343, No. 4, The Massachusetts Medical Society.

Shen, et al., The Effects of Surface Chemistry and Adsorbed Proteins on Monocyte/Macrophage Adhesion to Chemically Modified Polystyrene Surfaces, Journal of Biomedical Matter Research, 2001, pp. 336-345, vol. 57.

Sherwood, et al., Transcriptional Dynamics of Endodermal Organ Formation, Developmental Dynamics, 2009, pp. 29-42, vol. 238, Issue 1.

Shi et al., Inducing Embryonic Stem Cells to Differentiate into Pancreatic β Cells by a Novel Three-Step Approach with Activin a and All-Trans Retinoic Acid, Stem Cells, 2005, 656-662, 23, AlphaMed Press.

Schindler et al., A synthetic nanofibrillar matrix promotes in vivo-like organization and morphogenesis for cells in culture, Biomaterials, Apr. 18, 2005, 5624-5631, 26, Elsevier.

Shiraki et al., TGF-B Signaling Potentiates Differentiation of Embryonic Stem Cells to Pdx-1 Expressing Endodermal Cells, Genes to Cells, 2005, 503-516, 10, Blackwell Publishing Limited.

Shiraki, et al., Guided Differentiation of Embryonic Stem Cells into Pdx1-Expressing Regional-Specific Definitive Endoderm, Stem Cells, 2008, pp. 874-885, vol. 26.

Sidhu et al., Derivation of Three Clones from Human Embryonic Stem Cell Lines by FACS Sorting and Their Characterization, Stem Cells and Development, 2006, 61-69, 15, Mary Ann Liebert, Inc.

Simons, et al., Assembly of Protein Tertiary Structures from Fragments with Similar Local Sequences Using Simulated Annealing and Bayesian Scoring Functions, Journal of Molecular Biology, 1997, pp. 209-225, vol. 268.

Simons, et al., Improved Recognition of Native-Like Protein Structures Using a Combination of Sequence-Dependent and Sequence-Independent Features of Proteins, Proteins: Structure, Function, and Genetics, 1999, pp. 82-95, vol. 34, Wiley-Liss, Inc.

Skoudy et al., Transforming growth factor (TGF)β, fibroblast growth factor (FGF) and retinoid signalling pathways promote pancreatic exocrine gene expression in mouse embryonic stem cells, Journal of Biochemistry, 2004, 749-756, 379, Biochemical Society, GB.

Smith et al., Anti-Interleukin-6 Monocolnal Antibody Induces Regression of Human Prostate Cancer Xenografts in Nude Mice, the Prostate, Mar. 2, 2001, 47-53, 48, Wiley-Liss, Inc.

Soria et al., Insulin-Secreting Cells Derived From Embryonic Stem Cells Normalize Glycemia in Streptozotocin-Induced Diabetic Mice, Diabetes, Feb. 2000, 1-6, 49, American Diabetes Association.

Stadtfeld, et al., Defining Molecular Cornerstones During Fibroblast to iPS Cell Reprogramming in Mouse, Cell Stem Cell, Mar. 2008, pp. 230-240, vol. 2.

Stafford, et al., Retinoic Acid Signaling is Required for a Critical Early Step in Zebrafish Pancreatic Development, Current Biology, 2002, pp. 1215-1220, vol. 12, Issue 14.

Stephen D. De Rosa, 11-color, 13-parameter flow cytometry: Identification of . . . , Nature, Feb. 1, 2001, 245-248, 7-2, Nature Publishing Group, US.

Stojkovic et al., An Autogeneic Feeder Cell System That Efficiently Supports Growth of Undifferentiated Human Embryonic Stem Cells, Stem Cells, 2005, 306-314, 23, AlphaMed Press.

Sugiyama, et al., Conserved Markers of Fetal Pancreatic Epithelium Permit Prospective Isolation of Islet Progenitor Cells by FACS, PNAS, Jan. 2, 2007, pp. 175-180, vol. 104, No. 1.

Sugiyama, et al., Fluorescence-Activated Cell Sorting Purification of Pancreatic Progenitor Cells, Diabetes, Obesity and Metabolism, 2008, pp. 179-185, vol. 10, Supplement 4.

Suh, et al., Characterization of His-X3-His Sites in a-Helices of Synthetic Metal-Binding Bovine Somatotropin, Protein Engineering, 1991, pp. 301-305, vol. 4, No. 3.

Sulzbacher, et al., Activin A-Induced Differentiation of Embryonic Stem Cells into Endoderm and Pancreatic Progenitors—The Influence of Differentiation Factors and Culture Conditions, Stem Cell Rev, 2009, pp. 159-173, vol. 5.

Takahashi, et al., Homogenous Seeding of Mesenchymal Stem Cells into Nonwoven Fabric for Tissue Engineering, Tissue Engineering, 2003, pp. 931-938, vol. 9, No. 5.

Takahashi, et al., Induction of Pluripotent Stem Cells from Adult Human Fibroblasts by Defined Factors, Cell, 2007, pp. 861-872, vol. 131.

Takehara, et al., Rho-Associate Kinase Inhibitor Y-27632 Promotes Survival of Cynomolgus Monkey Embryonic Stem Cells, Molecular Human Reproduction, 2008, pp. 627-634, vol. 14, No. 11.

Tang, et al., Reprogramming Liver-Stem WB Cells into Functional Insulin-Producing Cells by Persistent Expression of Pdx1-and Pdx1-VP16 Mediated by Lentiviral Vectors, Laboratory Investigation, 2006, pp. 83-93, vol. 86.

Tannock, et al., Chemotherapy with Mitoxantrone Plus Prednisone or Prednisone Alone for Symptomatic Hormone-Resistant Prostate Cancer: A Canadian Randomized Trial With Palliative End Points, Journal of Clinical Oncology, 1996, 1756-1764, 14-6, American Society of Clinical Oncology, US.

Teare, et al., Cellular Attachment to Ultraviolet Ozone Modified Polystyrene Surfaces, Langmuir, 2000, pp. 2818-2824, vol. 16.

(56) References Cited

OTHER PUBLICATIONS

Thomson et al., Embryonic Stem Cell Lines Derived from Human Blastocysts, Science, Nov. 6, 1998, 1145-1147, 282, HighWire Press.
Thomson et al., Isolation of a primate embryonic stem cell line, Developmental Biology, Aug. 1995, 7844-7848, 92, Proc. Natl. Acad. Sci, US.
Thomson et al., Primate Embryonic Stem Cells, Currenl Topics in Developmental Biology, 1998, 133-154, 38, Academic Press, US.
Tomita, et al., Bone Marrow-Derived Stem Cells Can Differentiate into Retinal Cells in Injured Rat Retina, Stem Cells, 2002, pp. 279-283, vol. 20.
Tsai, et al., Isolation of Human Multipotent Mesenchymal Stem Cells from Second-Trimester Amniotic Fluid Using a Novel Two-Stage Culture Protocol, Human Reproduction, Apr. 22, 2004, pp. 1450-1456, vol. 19, No. 6.
Tulachan et al., TGF-β isoform signaling regulates secondary transition and mesenchymal-induced endocrine development in the embryonic mouse pancreas, Developmental Biology, 2007, 508-521, 305, Elsevier.
Ubeda et al., Inhibition of Cyclin-dependent Kinase 5 Activity Protects Pancreatic Beta Cells from Glucotoxicity, Journal of Biological Chemistry, Aug. 3, 2006, 28858-28864, 39, JBC Papers in Press.
Uludag, et al., Technology of Mammalian Cell Encapsulation, Advanced Drug Delivery Reviews, 2000, pp. 29-64, vol. 42.
Ungrin, et al., Reproducible, Ultra High-Throughput Formation of Multicellular Organization from Single Cell Suspension-Derived Human Embryonic Stem Cell Aggregates, Plos ONE, 2008, e1565, pp. 1-12, vol. 3, Issue 2.
Unknown, MeSH Descriptor Data, National Library of Medicine—Medical Subject Headings, Feb. 26, 1992, XP002553615.
Unknown, Preserve the Stability of Your Stem Cells, Stem Cells, 2006, Internet Citation, XP002496166.
Vacanti, et al., Selective Cell Transplantation Using Bioabsorbable Artificial Polymers as Matrices, Journal of Pediatric Surgery, Jan. 1988, 3-9, 23-1.
Valet, et al, Pretherapeutic Identification of High-Risk Acute Myeloid Leukemia (AML) Patients from . . . , Clinical Cytometry, Feb. 17, 2003, 4-10, 53B, Wiley-Liss, Inc., US.
Vallier, et al., Activin/Nodal and FGF Pathways Cooperate to Maintain Pluripotency of Human Embryonic Stem Cells, Journal of Cell Sciences, 2005, pp. 4495-4509, vol. 118.
Van Der Greef et al., Rescuing drug discovery: in vivo systems pathology and systems pharmacology, Nature, Dec. 1, 2005, 961-967, 4-1, Nature Reviews, US.
Van Der Windt, et al., The Chioce of Anatomical Site for Islet Transplantation, Cell Transplantation, 2008, pp. 1005-1014, vol. 17.
Van Kooten, et al., Plasma-Treated Polystyrene Surfaces: Model Surfaces for Studying Cell-Biomaterial Interactions, Biomaterials, 2004, pp. 1735-1747, vol. 25.
Van Wachem, et al., Vacuum Cell Seeding: a New Method for the Fast Application of an Evenly Distributed Cell Layer on Porous Vascular Grafts, Biomaterials, 1990, pp. 602-606, vol. 11.
Vanderford et al., Multiple kinases regulate mafA expression in the pancreatic beta cell line MIN6, Biochemistry and Biophysics, 2008, 138-142, 480, Elsevier.
Vodicka, et al., The Miniature Pig as an Animal Model in Biomedical Research, Annals New York Academy of Sciences, 2005, pp. 161-171, vol. 1049.
Vunjak-Novakovic, et al., Dynamic Cell Seeding of Polymer Scaffolds for Cartilage Tissue Engineering, Biotechnology Program, 1998, pp. 193-202, vol. 14, Issue 2.
Wang et al., Derivation and Growing Human Embryonic Stem Cells on Feeders Derived from Themselves, Stem Cells, 2005, 1221-1227, 23, AlphaMed Press.
Wang et al., Relationship of Chemical Structures of Anthraquinones with their Effects on the Suppression of Immune Responses, International Journal of Immunopharmacology, 1987, 733-739, 9-6, International Society for Immunopharmacology, GB.
Wang, et al., Noggin and bFGF Cooperate to Maintain the Pluripotency of Human Embryonic Stem Cells in the Absence of Feeder Layers, Biochemical and Biophysical Research Communications, 2005, pp. 934-942, vol. 33, No. 3.
Watanabe, et al., A Rock Inhibitor Permits Survival of Dissociated Human Embryonic Stem Cells, Nature Biotechnology, 2007, pp. 681-686, vol. 25, No. 6.
Wei et al., Cdk5-dependent regulation of glucose-stimulated insulin secretion, Nature Medicine, Sep. 11, 2005, 1104-1108, 11-10, Nature Publishing Group.
Wei, et al., Human Amnion-Isolated Cells Normalize Blood Glucose in Strepozotocin Induced Diabetic Mice, Cell Transplantation, 2003, pp. 545-552, vol. 12, No. 5.
Wei, et al., Transcriptome Profiling of Human and Murine ESCs Identifies Divergent Paths Required to Maintain the Stem Cell State, Stem Cells, 2005, pp. 166-185, vol. 23.
Wells, et al., Early Mouse Endoderm is Patterned by Soluble Factors from Adjacent Germ Layers, Development, 2000, pp. 1563-1572, vol. 127, Issue 8.
Wernig, et al., c-Myc is Dispensable for Direct Reprogramming of Mouse Fibroblasts, Cell Stem Cell, Jan. 2008, pp. 10-12, vol. 2.
Wiles et al., Embryonic Stem Cell Development in a Chemically Defined Medium, Experimental Cell Research, 1999, 241-248, 247, Academic Press.
Wilson, et al., The HMG Box Transcription Factor Sox4 Contributes to the Development of the Endcrine Pancreas, Diabetes, 2005, pp. 3402-4309, vol. 54, Issue 12.
XP002553616_1989, RecName: Full=lnhibin beta B Chain; AltName: Full=Activin beta-B chain; Flags; Precurso, Database UniProt [Online], Jul. 1, 1989, Database Accession No. P09529, EBI Accession No. Uniprot: P09529.
Xu et al., Immortalized Fibroblast-Like Cells Derived from Human Embryonic Stem Cells Support Undifferentiated Cell Growth, Stem Cells, 2004, 972-980, 22, AlphaMed Press.
Xu, et al., Basic FGF and Suppression of BMP Signalling Sustain Undifferentiated Proliferation of Human ES Cells, Nature Methods, 2005, pp. 185-189, vol. 2, Issue 3.
Xu, et al., Feeder-free Growth of Undifferentiated Human Embryonic Stem Cells, Nature Biotechnology, 2001, pp. 971-974, vol. 19.
Yang et al., Novel cell immobilization method utilizing centrifugal force to achieve high-density hepatocyte culture in porous scaffold, Journal of Biomed Materials Research, Feb. 27, 2001, 379-386, 55, John Wiley & Sons, Inc.
Yang, et al., Survival of Pancreatic Islet Xenografts in NOD Mice with the Theracyte Device, Transplantation Proceedings, 2002, pp. 3349-3350, vol. 34.
Yasuda, et al., Development of Cystic Embryoid Bodies with Visceral Yolk-Sac-Like Structures from Mouse Embryonic Stem Cells Using Low-Adherence 96-Well Plate, Journal of Bioscience and Bioengineering, Apr. 4, 2009, pp. 442-446, vol. 107, No. 4.
Yoneda, et al., The Rho Kinases I and II Regulate Different Aspects of Myosin II Acitivity, The Journal of Cell Biology, 2005, pp. 443-445, vol. 170, No. 3.
Young, et al, Three-Dimensional Culture of Human Uterine Smooth Muscle Nyocytes on a Resorbably Scaffolding, Tissue Engineering, 2003, pp. 451-459, vol. 9, No. 3.
Yu, et al., Induced Pluripotent Stem Cell Lines Derived from Human Somatic Cells, Science, Dec. 21, 2007, pp. 1917-1920, vol. 318.
Yu, et al., Isolation of a Novel Population of Multipotent Adult Stem Cells from Human Hair Follicles, American Journal of Pathology, Jun. 6, 2006, pp. 1879-1888, vol. 168, No. 6.
Zembower, et al., Peptide Boronic Acids Versatile Synthetic Ligands for Affinity Chromatography of Serine Proteinases, International Journal Peptide Protein, 1996, pp. 405-413, vol. 47.
Zhang et al., MafA is a Key Regulator of Glucose-Stimulated Insulin Secretion, Molecular and Cellular Biology, Jun-2005, 4969-4976, 25-12, American Society for Microbiology.
Zhang, et al., Differentiation Potential of Bone Marrow Mesenchymal Stem Cells into Retina in Normal and Laser-Injured Rat Eye, Science in China Series, 2004, pp. 241-250, vol. 47, No. 3.
Zhang, Jie, The Differentiation of Bone Marrow Mesenchymal Stem Cells into Retina in Rat Eye and the Therapeutical Effect on Severe Injured Retina, a Doctoral Thesis of Chinese PLA Acadamey of Military Medical Sciences, 2003, 1-127, 1-127 (with English Abstract).

(56) References Cited

OTHER PUBLICATIONS

Zhang, et al., Highly Efficient Differentiation of Human ES Cells and iPS Cells into Mature Pancreatic Insulin-Producing Cells, Cell Research, 2009, pp. 429-438, vol. 19, Issue 14.
Zhao et al., The Islet B Cell-enriched MafA Activator is a Key Regulator of Insulin Gene Transcription, Journal of Biological Chemistry, Mar. 25, 2005, 11887-11894, 280-12, The Amerian Society for Biochemistry and molecular Biology, Inc.
Zhao, et al., Derivation and Characterization of Hepatic Progenitor Cells from Human Embryonic Stem Cells, PLoS One Hepatic Progenitors from hESCs, Jul. 2009, e6468 pp. 1-10, vol. 4, Issue 7.
Zorn, et al., Vertebrate Endoderm Development and Organ Formation, Annual Review Cell Development Biology, 2009, pp. 221-251, vol. 25.
Zubaty, et al., Transplantation of Mesenchymal Stem Cells into RCS Rats for Retinal Repair, Investigative Ophthalmology and Visual Science, 2005, pp. 4160-B518, vol. 46, Supplement S.
Chen, et al., Retinoic Acid Signaling is Essential for Pancreas Development and Promotes Endocrine at the Expense of Exocrine Cell Differentiation in Xenopus, Developmental Biology, 2004, pp. 144-160, vol. 271.
Gregg Duester, Retinoic Acid Synthesis and Signaling During Early Organogenesis, Cell, 2008, pp. 921-931, vol. 134.
Rezania, E Al., Maturation of Human Embryonic Stem Cell-Derived Pancreatic Progenitors Into Functional Islets Capable of Treating Pre-Existing Diabetes in Mice, Diabetes, 2012, pp. 2016-2029, vol. 61.
Ross, et al., Cytochrome P450s in the Regulation of Cellular Retinoic Acid Metabolism, Annu. Rev. Nutr., 2011, pp. 65-87, vol. 31.
Simandi, et al., Retinoid Signaling is a Context-Dependent Regulator of Embryonic Stem Cells, Embryonic Stem Cells—Differentiation and Pluripotent Alternatives, 2011, pp. 55-79, Chapter 3.
Stafford, et al., Retinoids Signal Directly to Zebrafish Endoderm to Specify Insulin-Expressing B-cells, Development, 2005, pp. 949-956, vol. 133.
White, et al., Complex Regulation of cyp26a1 Creates a Robust Retinoic Acid Gradient in the Zebrafish Embryo, Plos Biology, 2007, pp. 2522-2533, vol. 5, Issue 11.
Abe, et al., Evidence That P13K, Rac, Rho, and Rho Kinase are Involved in Basic Fibroblast Growth Factor-Stimulated Fibroblast-Collagen Matrix Contraction, Journal of Cellular Biochemistry, 2007, pp. 1290-1299, vol. 102.
Ali, et al., Exploitation of Protein Kinase C: A Useful Target for Cancer Therapy, Cancer Treatment Reviews, 2009, pp. 1-8, vol. 35.
Assady, et al., Insulin Production by Human Embryonic Stem Cells, Diabetes, 2001, pp. 1691-1697, vol. 50.
Bai, et al., Glucagon-Like Peptide-1 Enhances Production of Insulin in Insulin-Producing cells Derived from Mouse Embryonic Stem Cells, Journal of Endocrinology, 2005, pp. 343-352, vol. 186, No. 2.
Bandyopadhyay, et al., Inhibition of Pulmonary and Skeletal Metastasis by a Transforming Growth Factor-B Type I Receptor Kinase Inhibitor, Cancer Research, 2006, pp. 6714-6721, vol. 66, No. 13.
Bellinger, et al., Swine Models of Type 2 Diabetes Mellitus: Insulin Resistance, Glucose Tolerance, and Cardiovascular Complications, ILAR Journal, 2006, pp. 243-258, vol. 47, No. 3.
Best, et al., Embryonic Stem Cells to Beta-Cells by Understanding Pancreas Development, Molecular and Cellular Endorinology, 2008, pp. 86-94, vol. 288.
Bo, et al., Research Progress of Pancreatic Islet Development and Pancreatic Stem Cells, Journal of Clinical Surgery, 2009, pp. 208-210, vol. 17, No. 3.
Brevini et al, Embryonic Stem Cells in Domestic Animals, Theriogenology, 2010, pp. 544-550, vol. 74.
Chen, et al., Differentiation of Embryonic Stem Cells Towards Pancreatic Progenitor Cells and their Transplantation into Strepozotocin-Induced Diabetic Mice, Cell Biology International, 2008, pp. 456-461, vol. 32.
Chetty, et al., A Simple Tool ti Improve Pluripotent Stem Cell Differentiation, Nature Methods, 2013, pp. 553-558, vol. 10, No. 6.

Choi, et al., In Vitro Trans-Differentiation of Rat Mesenchymal Cells into Insulin-Producing Cells by Rat Pancreatic Extract, Biochemical and Biophysical Research Communications, 2005, pp. 1299-1305, vol. 330.
D'Amour et al, Production of pancreatic hormone, Nature Biotechnology, 2006, pp. 1392-1401, vol. 24.
Dekker, et al., Adhesion of Endothelial Cells and Adsorption of Serum Proteins on Gas Plasma-Treated Polytetrafluoroethylene, Biomaterials, 1991, pp. 130-138, vol. 12.
Deramaudt, et al., The PDX1 Homeodomain Transcription Factor Negatively Regulates the Pancreatic Ductal Cell-specific Keratin 19 Promoter*, Journal of Biological Chemistry, 2006, pp. 38385-38395, vol. 281, No. 50.
Dufour, et al., Development of an Ectopic Site for Islet Transplantation Using Biodegradable Scaffolds, Tissue Engineering, 2005, pp. 1323-1331, vol. 11, No. 9/10.
Florio, et al., Activin A Stimulates Insulin Secretion in Cultured Human Pancreatic Islets, J. Endocrinol. Invest., 2000, pp. 231-234, vol. 23.
Foster, et al., Differentiation of Transplanted Microencapsulated Fetal Pancreatic Cells, Experimental Transplantation, Jun. 15, 2007, pp. 1440-1448, vol. 83, No. 11.
Gellibert, et al., Identification of 1,5-Naphthyridine Derivatives as a Novel Series of Potent and Selective TGF-B Type I Receptor Inhibitor, J. Med. Chem, 2004, pp. 4494-4506, vol. 47, No. 18.
Gibco, Solutions for Life Science Research and Drug Discovery, Catalogue Cell Culture Products, 2004-2005, pp. 1-4E, 281406 26 5 27.
Gittest, Developmental Biology of the Pancreas: A comprehensive Review, Developmental Biology, 2009, pp. 4-35, vol. 326, No. 1.
Gordon Weir, Do stem cells hold the key to creation of a cure for diabetes?, Diabetes Voice, 2008, pp. 29-31, Edition 53, No. 2.
Hainsworth, et al., Retinal Capillar Basement Membrane Thickening in a Porcine Model of Diabetes Mellitus, Comp Med, 2002, pp. 523-529, vol. 52.
Hay, et al., Highly Effificient Differentiation of hESCs to Functional Hepatic Endoderm Requires ActivinA and Wnt3a Signaling, PNAS, 2008, pp. 12301-12306, vol. 105, No. 34.
Heinis, et al., HIF1a and Pancreatic Beta-Cell Development, The FASEB Journal, 2012, pp. 2734-2742, vol. 26.
Heinis, et al., Oxygen Tension Regulates Pancreatic Beta-Cell Differentiation Through Hypoxia-Inducible Factor 1x, Diabetes, 2010, pp. 662-669, vol. 59.
Heit, et al., Embryonic Stem Cells and Islet Replacement in Diabetes Mellitus, Pediatric Diabetes, 2004, pp. 5-15, vol. 5.
Heremans, et al., Recapitulation of Embryonic Neuroendocrine Differentiation in Adult Human Pancreatic Duct Cells Expressing Neurogenin 3, The Journal of Cell Biology, 2002, pp. 303-311, vol. 159.
Herrera, Adult-Insulin-and Glucagon-Producing Cells Differentiate from Two Independent Cell Lineages, Development, 2000, pp. 2317-2322, vol. 127, No. 11.
Hoffman, et al., Characterization and Culture of Human Embryonic Stem Cells, Nature Biotechnology, 2005, pp. 699-708, vol. 23, No. 6.
Hosoya, et al., Induction of Differentiation of Undifferentiated Cells into Pancreatic Beta-Cells in Vertebrates, Int. J. Dev. Biol., 2012, pp. 313-323, vol. 56.
Inman, et al., SB-431542 is a Potent and Specific Inhibitor of Transforming Growth Factor-B Superfamily Type I Activing Receptor-Like Kinase (ALK) Receptors ALK4, ALK5, and ALK7, Molecular Pharmacology, 2002, pp. 65-74, vol. 62, No. 1.
Itkin-Ansari, et al., Cell-Based Therapies for Diabetes: Progress Towards a Transplantable Human B Cell Line, Annals of the New York Academy of Sciences, 2003, pp. 138-147, vol. 1005, No. 1.
Karvonen, et al., Incidence of Childhood Type 1 Diabetes Woldwide, Diabetes Care, 2000, pp. 1516-1526, vol. 23, No. 10.
Konstantinova, et al., EphA-Ephrin-A-Mediated Beta Cell Communication Regulates Insulin Secretion from Pancreatic Islets, Cell, Apr. 20, 2007, pp. 359-370, vol. 129.
Kozikowski, et al., New Amide-Bearing Benzolactam-Based Protein Kinase C Modulators Induce Enhanced Secretion of the Amyloid Precuros Protein Metabolite sAPPa, J. Med. Chem., 2003, pp. 364-373, vol. 46, No. 3.

(56) References Cited

OTHER PUBLICATIONS

Kurihara-Bergstrom, et al., Characterization of the Yucatan Miniature Pig Skin and Small Intestine for Pharmaceutical Applications, Laboratory Animal Science, 1986, pp. 396-399, vol. 36, No. 4.

Larsen, et al., Use of the Gootingen Minipig as a Model of Diabetes, with Special Focus on Type 1 Diabetes Research, ILAR Journal, 2004, pp. 303-313, vol. 45, No. 3.

Lee, et al., PKC—Inhibitors Sustain Self-Renewal of Mouse Embryonic Stem Cells Under Hypoxia in Vitro, Experimental and Molecular Medicine, Apr. 2010, pp. 294-301, vol. 43, No. 4.

Lee, et al., Protein Kinase A- and C-Induced Insulin Release from Ca2+-Insensitive Pools, Cellular Signalling, 2003, pp. 529-537, vol. 15.

Leon-Quinto, et al., In Vitro Directed Differentiation of Mouse Embryonic Stem Cells into Insulin-Producing Cells, Diabetologia, 2004, pp. 1442-1451, vol. 47, No. 8.

Li, et al., Pluripotency Can be Rapidly and Efficiently Induced in Human Amniotic Fluid-Derived Cells, Human Molecular Genetics, 2009, pp. 4340-4349, vol. 18, No. 22.

Mao, et al., The Reversal of Hyperglycaemia in Diabetic Mice Using PLGA Scaffolds Seeded with Islet-like Cells Derived from Human Embyonica Stem Cells, Biomaterials, 2009, pp. 1706-1714, vol. 30.

Mathis, et al., B-Cell Death During Progression to Diabetes, Nature, 2001, pp. 792-798, vol. 414.

Matveyenko, et al., Inconsistent Formation and Nonfunction of Insulin-Positive Cells from Pancreatic Endoderm Derived from Human Embryonic Stem Cells in Athymic Nude Rats, American Journal of Physiol Endocrinol Metab, 2010, pp. E713-E720, vol. 299.

Munoz et al, Conventional pluripotency markers, Theriogenology, 2008, pp. 1159-1164, vol. 69.

Nelson, et al., The Transcription Factors Nkx6.1 and Nkx6.2 Possess Equivalent Activities in Promoting Beta-Cell Fate Specification in Pdx1+ Pancreatic Progenitor Cells, Development, 2007, pp. 2491-2500, vol. 134.

Odom, et al., Control of Pancreas and Liver Gene Expression by HNF Transcription Factors, Science, 2004, pp. 1378-1381, vol. 303, No. 5662.

Ouziel-Yahalom, et al., Expansion and Redifferentiation of Adult Human Pancreatic islet Cells, Biochemical and Biophysical Research Communications, 2006, pp. 291-298, vol. 341.

Paris, et al, Embryonic Stem Cells in Domestic Animals, Theriogenology, 2010, pp. 516-524, vol. 74.

Perrier, et al., Derivation of Midbrain Dopamine Neurons from Human Embryonic Stem Cells, PNAS, Aug. 24, 2004, pp. 12543-12548, vol. 101, No. 34.

Phillips, et al., Directed Differentiation of Human Embryonic Stem Cells into the Pancreatic Endocrine Lineage, Stem Cells and Development, 2007, pp. 561-578, vol. 16, No. 4.

Ptasznik, et al., Phosphatidylinositol 3-Kinase is a Negative Regulator of Cellular Differentiation, The Journal of Cell Biology, 1997, pp. 1127-1136, vol. 137, No. 5.

R&D Systems, Embryonic & Induced Pluripotent Stem Cell Transcription Factors, Embryonic & Induced Pluripotent Stem Cell Transcription Factors, 2013, http://www.mdsystems.com/molecule_group.aspx?r=1&g-3041, 2 page web printout.

R&D Systems, Pancreatic Endoderm, Pancreatic Endoderm, Jun. 24, 2013, http://www.rndsystems.com/molecule_group.aspx?g=801&r, 1 page web printout.

Ramiya, et al., Reversal of Insulin-Dependent Diabetes Using Islets Generated in vitro from Pancreatic Stem Cells, Nature Medicine, 2000, pp. 278-281, vol. 6.

Rezania, et al., Maturation of Human Embryonic Stem Cell-Derived Pancreatic Progenitors into Functional Islets Capable of Treating Pre-Existing Diabetes in Mice, Diabetes, 2012, pp. 2016-2029, vol. 61.

Sander, et al., Homeobox Gene Nkk6.1 Lies Downstream of Nkx2.2 in the Major Pathway of Betta-Cell Formation in the Pancreats, Development, 2000, pp. 5533-5540, vol. 127.

Schisler, et al., The Nkx6.1 Homeodomain Transcription Factor Suppresses Glucagon Expression and Regulates Glucose-Stimulated Insulin Secretion in Islet Beta Cells, Proceedings of the National Academy of Sciences of the USA, 2005, pp. 7297-7302, vol. 102, No. 20.

Schnier, et al., G1 Arrest and Down-Regulation of Cyclin E/cyclin-dependent Kinase 2 by the Protein Kinase Inhibitor Staurosporine are Dependent on the Retinoblastoma Protein in the Bladder Carcinoma Cell Line 5637, Proceedings of the National Academy of Sciences, 1996, pp. 5941-5946, vol. 93.

Schuldiner, et al., Induced Neuronal Differentiation of Human Embryonic Stem Cells, Brain Research, 2001, pp. 201-205, vol. 913.

Serafimidis, et al., Novel Effectors of Directed and Ngn3-Mediated Differentiation of Mouse Embryonic Stem Cells into Endocrine Pancreas Progenitors, Stem Cells, 2008, pp. 3-16, vol. 26.

Shim, et al., Directed Differentiation of Human Embryonic Stem Cells Towards a Pancreatic Cell Fate, Diabetologia, 2007, pp. 1228-1238, vol. 50.

Soria, et al., From Stem Cells to Beta Cells: New Strategies in Cell Therapy of Diabetes Mellitus, Diabetologia, 2001, pp. 407-415, vol. 44.

Soria, et al., Insulin-Secreting Cells Derived From Embryonic Stem Cells Normalize Glycemia in Streptozotocin-Induced Diabetic Mice, Diabetes, 2000, pp. 157-162, vol. 49, No. 2.

Spence, et al., Translation Embryology: Using Embryonic Principles to Generate Pancreatic Endocrine Cells from Embryonic Stem Cells, Developmental Dynamics, 2007, pp. 3218-3227, vol. 236.

Stoffel, et al., Navigating the Pathway from Embryonic Stem Cells to Beta Cells, Seminars in Cell & Developmental Biology, 2004, pp. 327-336 vol. 15.

Sun, et al., Feeder-Free Derivation of Induced Pluripotent Stem Cells from Adult Human Adipose Stem Cells, Proceedings and the National Academy of Sciences, 2009, pp. 15720-15725, vol. 106, No. 37.

Suzuken, Differentiation of Multifunctional Stem Cells Using Human Feeder Cells, Research Papers of the Suzuken Memorial Foundation, 2007, pp. 193-197, vol. 24, JP.

Swindle, et al., Swine in Biomedical Research: Management and Models, ILAR News, 1994, pp. 1-5, vol. 36, No. 1.

Totonchi, et al., Feeder-and Serum-Free Establishment and Expansion of Human Induced Pluripotent Stem Cells, Int. J. Dev. Biol., 2010, pp. 877-886, vol. 54.

Tsuchida, et al., Activin Isoforms Signal Through Type I Receptor Serine/Threonin Kinase ALK7, Molecular and Cellular Endocrinology, 2004, pp. 59-65, vol. 22.

Verfaillie, et al., Stem Cells: Hype and Reality, Hematology, 2002, pp. 369-391.

Wong, et al., Directed Differentiation of Human Pluripotent Stem Cells into Mature Airway Epithelial Expressing Functional CFTR Protein, Nature Biotechnology, 2012, pp. 876-884, vol. 30, No. 9.

Xudong, et al., Research Progress in Inducing Stem Cels to Differentiate toward the B-like Cells of Pancreatic Islet, Chinese Bulletin of Life Sciences, 2007, pp. 526-530, vol. 19, No. 5 (English Abstract).

* cited by examiner

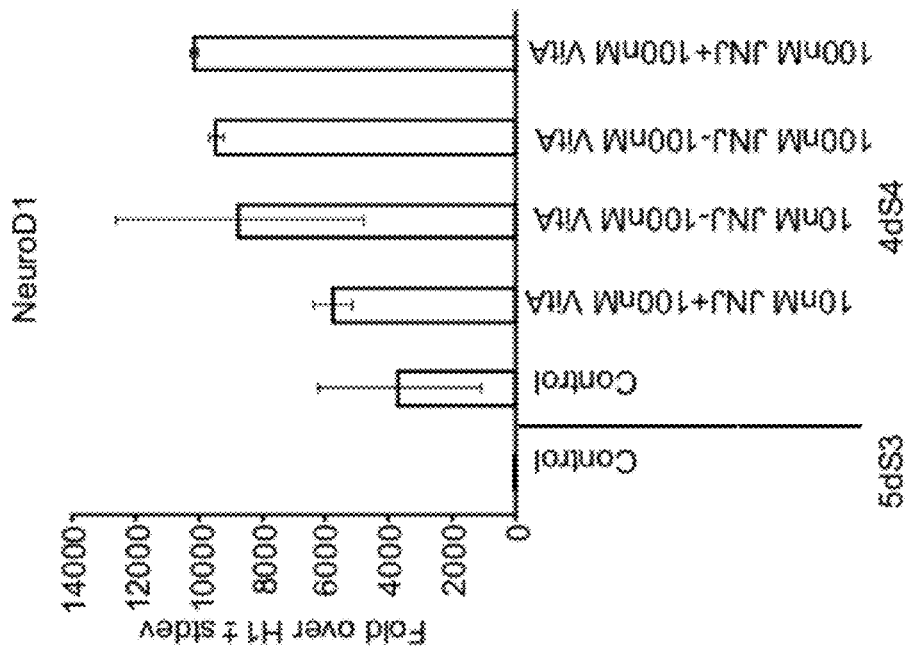
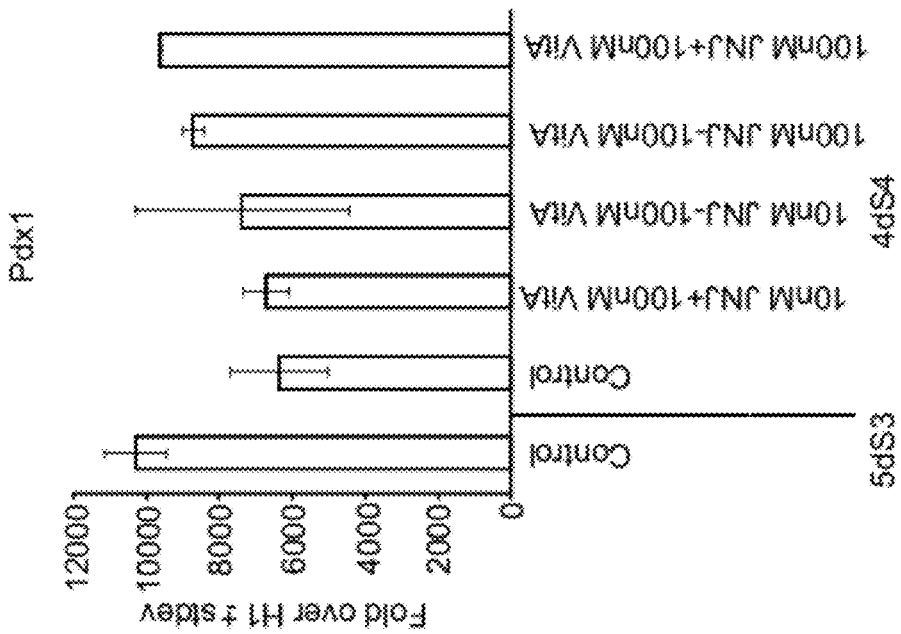

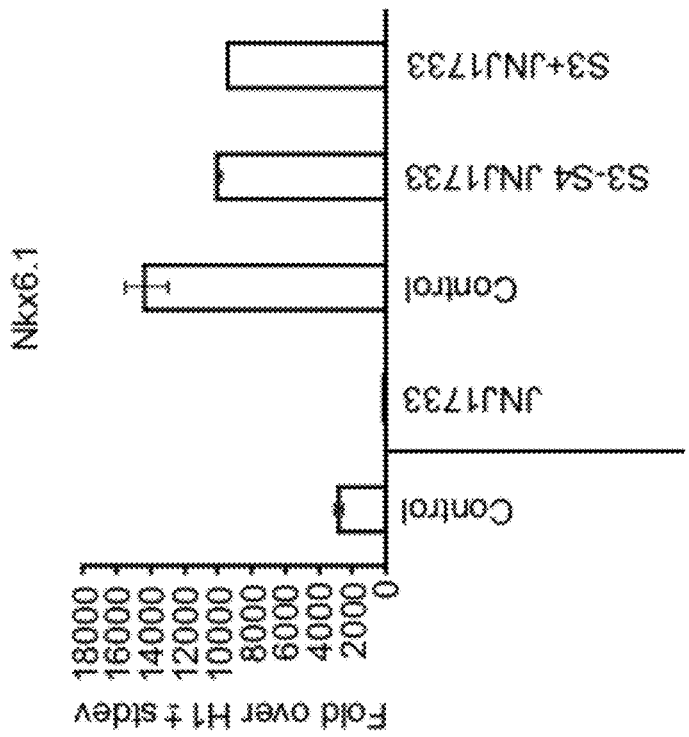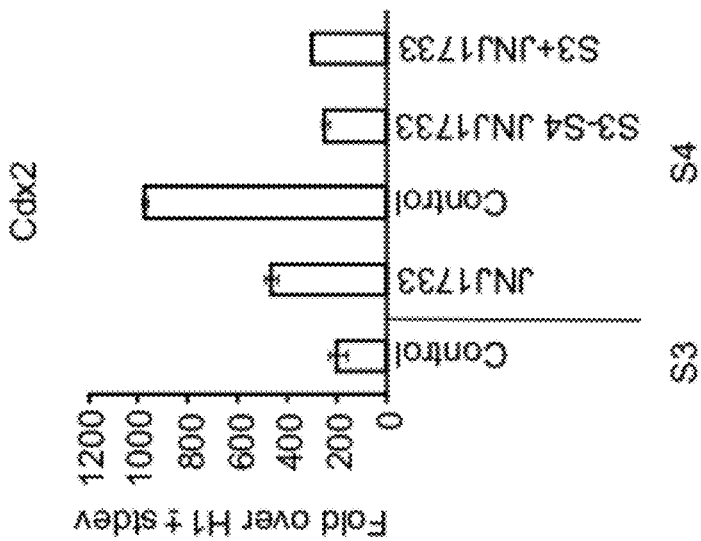

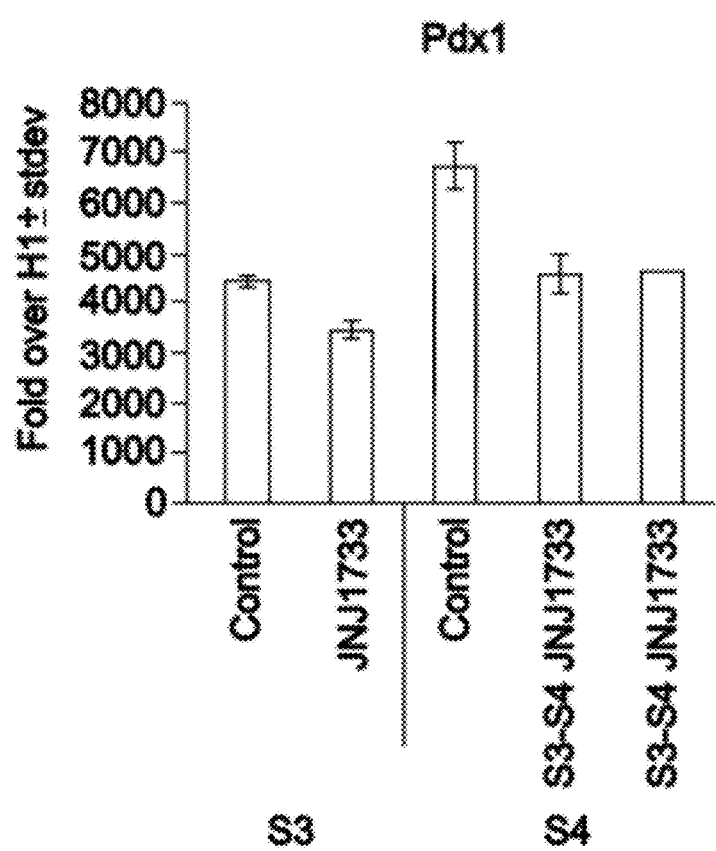

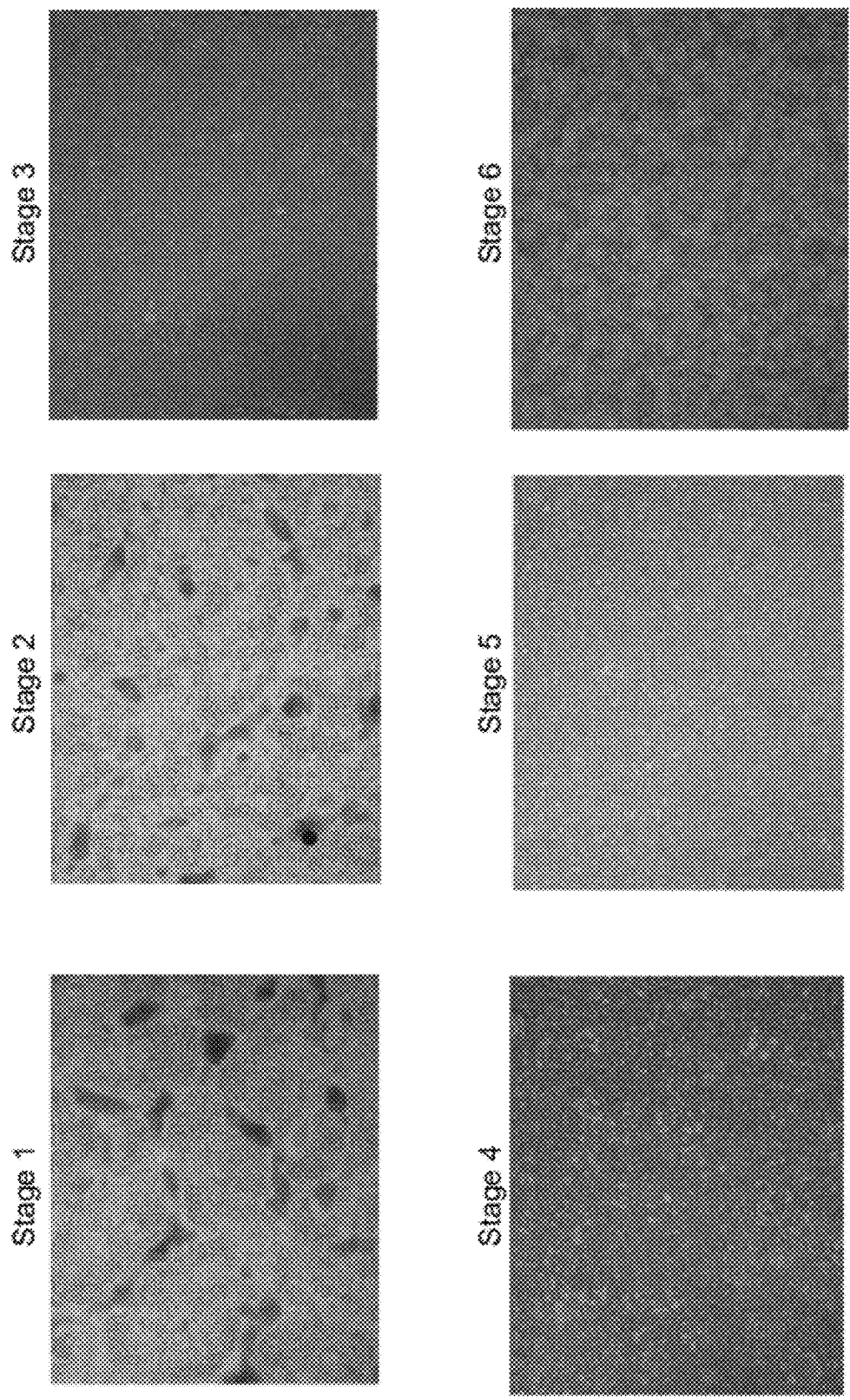

DIFFERENTIATION OF PLURIPOTENT STEM CELLS

CROSS REFERENCE TO RELATED APPLICATION

The present application claims the benefit of U.S. Provisional Patent Application Ser. No. 61/378,480, filed Aug. 31, 2010, which is incorporated herein by reference in its entirety for all purpose.

FIELD OF THE INVENTION

The present invention provides methods to promote the differentiation of pluripotent stem cells into insulin producing cells. In particular, the present invention provides a method utilizing a CYP26A inhibitor to produce a population of pancreatic endocrine precursor cells.

BACKGROUND

Advances in cell-replacement therapy for Type I diabetes mellitus and a shortage of transplantable islets of Langerhans have focused interest on developing sources of insulin-producing cells, or β cells, appropriate for engraftment. One approach is the generation of functional β cells from pluripotent stem cells, such as, for example, embryonic stem cells.

In vertebrate embryonic development, a pluripotent cell gives rise to a group of cells comprising three germ layers (ectoderm, mesoderm, and endoderm) in a process known as gastrulation. Tissues such as, for example, thyroid, thymus, pancreas, gut, and liver, will develop from the endoderm, via an intermediate stage. The intermediate stage in this process is the formation of definitive endoderm. Definitive endoderm cells express a number of markers, such as, HNF3 beta, GATA4, MIXL1, CXCR4 and SOX17.

Formation of the pancreas arises from the differentiation of definitive endoderm into pancreatic endoderm. Cells of the pancreatic endoderm express the pancreatic-duodenal homeobox gene, PDX1. In the absence of PDX1, the pancreas fails to develop beyond the formation of ventral and dorsal buds. Thus, PDX1 expression marks a critical step in pancreatic organogenesis. The mature pancreas contains, among other cell types, exocrine tissue and endocrine tissue. Exocrine and endocrine tissues arise from the differentiation of pancreatic endoderm.

Pancreatic development in vivo relies, at least in part, upon appropriate regulation of the signals that specify organ progenitor fields. Kinkel et al (PNAS May 12, 2009 vol. 106 no. 19 7864-7869) state "Pancreatic cell fates are specified by retinoic acid (RA), and proper size and localization of the pancreatic field are dependent on tight control of RA signaling. Here we show that the RA-degrading Cyp26 enzymes play a critical role in defining the normal anterior limit of the pancreatic field."

Cells bearing the features of islet cells have reportedly been derived from embryonic cells of the mouse. For example, Lumelsky et al. (Science 292:1389, 2001) report differentiation of mouse embryonic stem cells to insulin-secreting structures similar to pancreatic islets. Soria et al. (Diabetes 49:157, 2000) report that insulin-secreting cells derived from mouse embryonic stem cells normalize glycemia in streptozotocin-induced diabetic mice.

In one example, Hori et al. (PNAS 99: 16105, 2002) disclose that treatment of mouse embryonic stem cells with inhibitors of phosphoinositide 3-kinase (LY294002) produced cells that resembled β cells.

In another example, Blyszczuk et al. (PNAS 100:998, 2003) reports the generation of insulin-producing cells from mouse embryonic stem cells constitutively expressing Pax4.

Micallef et al. reports that retinoic acid can regulate the commitment of embryonic stem cells to form PDX1 positive pancreatic endoderm. Retinoic acid is most effective at inducing Pdx1 expression when added to cultures at day 4 of embryonic stem cell differentiation during a period corresponding to the end of gastrulation in the embryo (Diabetes 54:301, 2005).

Miyazaki et al. reports a mouse embryonic stem cell line over-expressing Pdx1. Their results show that exogenous Pdx1 expression clearly enhanced the expression of insulin, somatostatin, glucokinase, neurogenin3, p48, Pax6, and Hnf6 genes in the resulting differentiated cells (Diabetes 53: 1030, 2004).

Skoudy et al. reports that activin A (a member of the TGF-β superfamily) upregulates the expression of exocrine pancreatic genes (p48 and amylase) and endocrine genes (Pdx1, insulin, and glucagon) in mouse embryonic stem cells. The maximal effect was observed using 1 nM activin A. They also observed that the expression level of insulin and Pdx1 mRNA was not affected by retinoic acid; however, 3 nM FGF7 treatment resulted in an increased level of the transcript for Pdx1 (Biochem. J. 379: 749, 2004).

Shiraki et al. studied the effects of growth factors that specifically enhance differentiation of embryonic stem cells into PDX1 positive cells. They observed that TGF-β2 reproducibly yielded a higher proportion of PDX1 positive cells (Genes Cells. 2005 June; 10(6): 503-16.).

Gordon et al. demonstrated the induction of brachyury [positive]/HNF3 beta [positive] endoderm cells from mouse embryonic stem cells in the absence of serum and in the presence of activin along with an inhibitor of Wnt signaling (US 2006/0003446A1).

Gordon et al. (PNAS, Vol 103, page 16806, 2006) states "Wnt and TGF-beta/nodal/activin signaling simultaneously were required for the generation of the anterior primitive streak".

However, the mouse model of embryonic stem cell development may not exactly mimic the developmental program in higher mammals, such as, for example, humans.

Thomson et al. isolated embryonic stem cells from human blastocysts (Science 282:114, 1998). Concurrently, Gearhart and coworkers derived human embryonic germ (hEG) cell lines from fetal gonadal tissue (Shamblott et al., Proc. Natl. Acad. Sci. USA 95:13726, 1998). Unlike mouse embryonic stem cells, which can be prevented from differentiating simply by culturing with Leukemia Inhibitory Factor (LIF), human embryonic stem cells must be maintained under very special conditions (U.S. Pat. No. 6,200,806; WO 99/20741; WO 01/51616).

D'Amour et al. describes the production of enriched cultures of human embryonic stem cell-derived definitive endoderm in the presence of a high concentration of activin and low serum (Nature Biotechnology 2005). Transplanting these cells under the kidney capsule of mice resulted in differentiation into more mature cells with characteristics of some endodermal organs. Human embryonic stem cell-derived definitive endoderm cells can be further differentiated into PDX1 positive cells after addition of FGF-10 (US 2005/0266554A1).

D'Amour et al. (Nature Biotechnology-24, 1392-1401 (2006)) states: "We have developed a differentiation process that converts human embryonic stem (hES) cells to endocrine cells capable of synthesizing the pancreatic hormones insulin, glucagon, somatostatin, pancreatic polypeptide and ghrelin. This process mimics in vivo pancreatic organogenesis by directing cells through stages resembling definitive endoderm, gut-tube endoderm, pancreatic endoderm and endocrine precursor en route to cells that express endocrine hormones".

In another example, Fisk et al. reports a system for producing pancreatic islet cells from human embryonic stem cells (US2006/0040387A1). In this case, the differentiation pathway was divided into three stages. Human embryonic stem cells were first differentiated to endoderm using a combination of sodium butyrate and activin A. The cells were then cultured with TGF-β antagonists such as Noggin in combination with EGF or betacellulin to generate PDX1 positive cells. The terminal differentiation was induced by nicotinamide.

There still remains a significant need to develop in vitro methods to generate a functional insulin expressing cell, that more closely resemble a β cell. The present invention takes an alternative approach to improve the efficiency of differentiating pluripotent stem cells toward insulin expressing cells, by generating a population of pancreatic precursor cells utilizing an agent that degrades retinoic acid.

SUMMARY

In one embodiment, the present invention provides a method utilizing a CYP26A inhibitor to produce a population of pancreatic endocrine precursor cells.

In one embodiment, formation of the population of pancreatic endocrine precursor cells is achieved utilizing a stepwise differentiation protocol, wherein a population of pluripotent stem cells is first differentiated into a population of cells expressing markers characteristic of the definitive endoderm lineage. Next, the population of cells expressing markers characteristic of the definitive endoderm lineage is then differentiated into a population of primitive gut tube cells. Next, the population of primitive gut tube cells is then differentiated into a population of posterior foregut cells. Next, the population of posterior foregut cells is then differentiated into a population of endocrine precursor cells by treating the population of posterior foregut cells with a medium supplemented with a CYP26A inhibitor.

In one embodiment, the population of endocrine precursor cells is further differentiated into a population of cells expressing markers characteristic of the pancreatic endocrine lineage.

BRIEF DESCRIPTION OF THE DRAWINGS

FIG. 3 shows phase images of cells at stages I-VI of protocol outlined in Example 3.

DETAILED DESCRIPTION

Figure 1A:
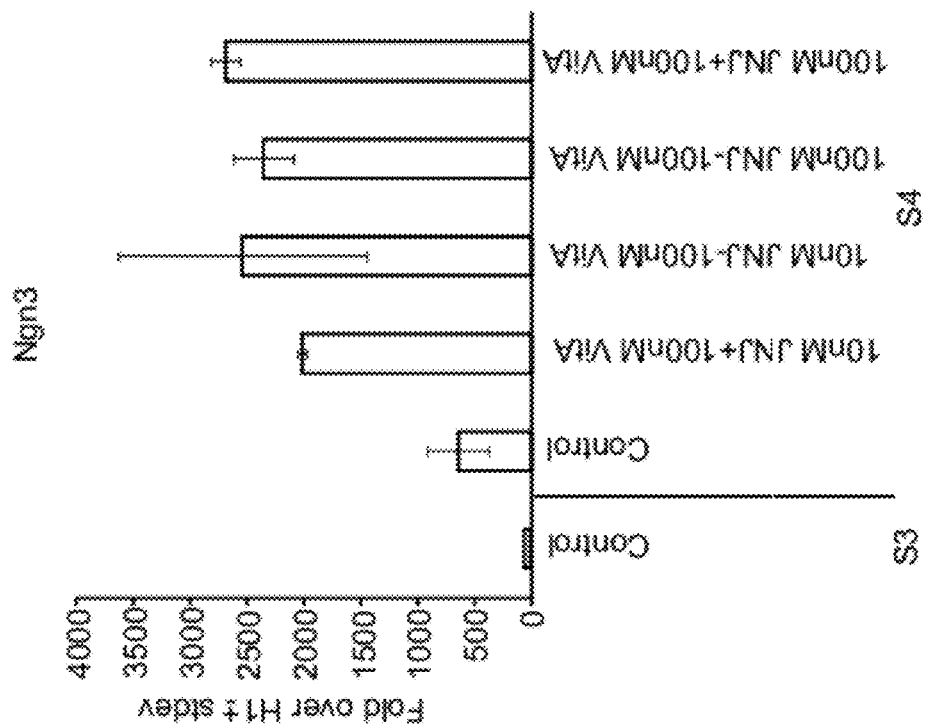
FIG. 1 shows real-time PCR data obtained from samples obtained from cells at stages III-IV, of the protocol outlined in Example 1, for a) PAX4, b) NGN3, c) PDX1, d) NEUROD, e) NKX6.1, f) CDX2, and g) Albumin. The y-axis is fold expression over undifferentiated H1 cells. Panel h shows NGN3 immunostaining for control and CYP26A treated cultures at stage IV.
Figure 1B:
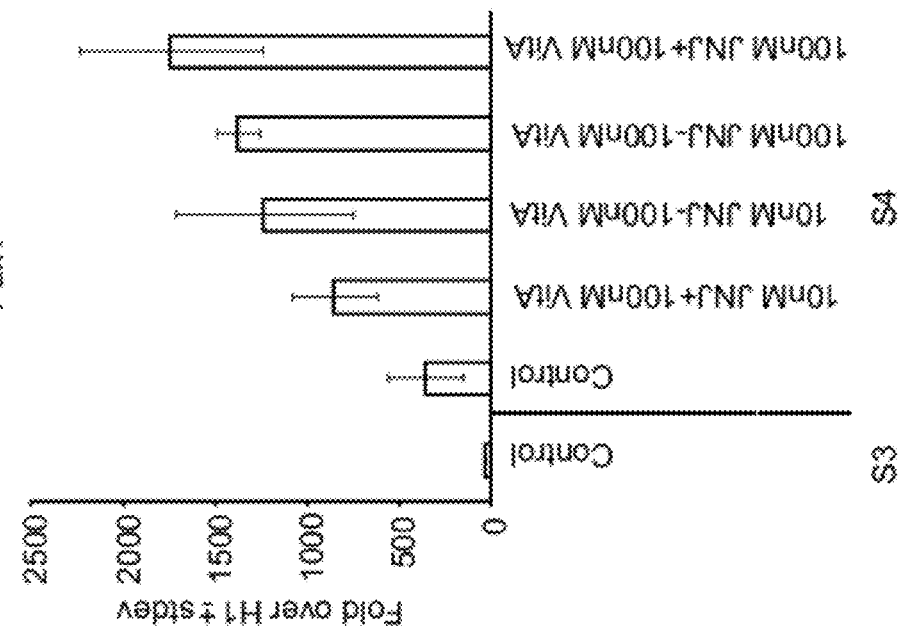
Figure 1F:
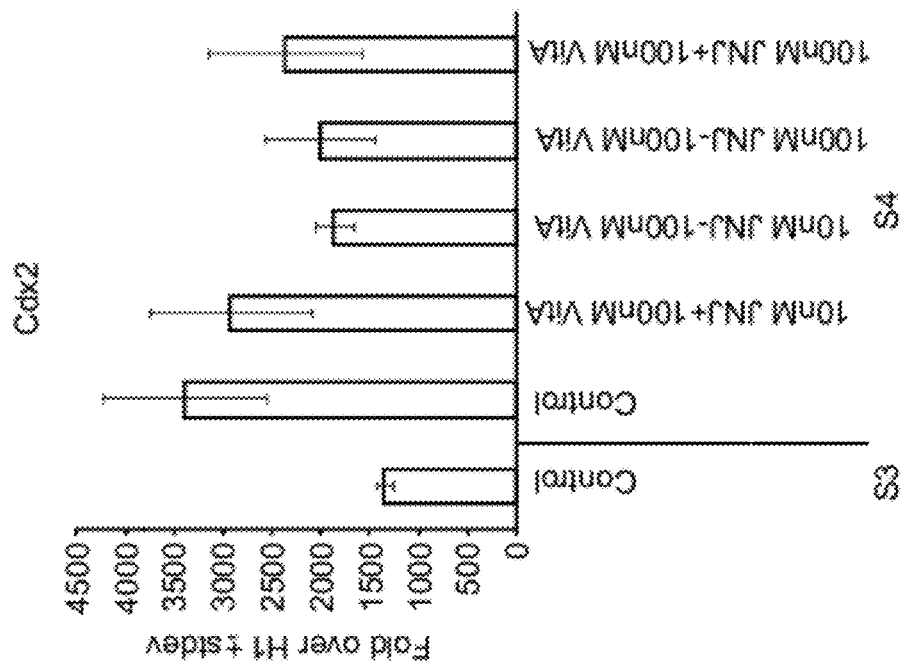
Figure 1E:
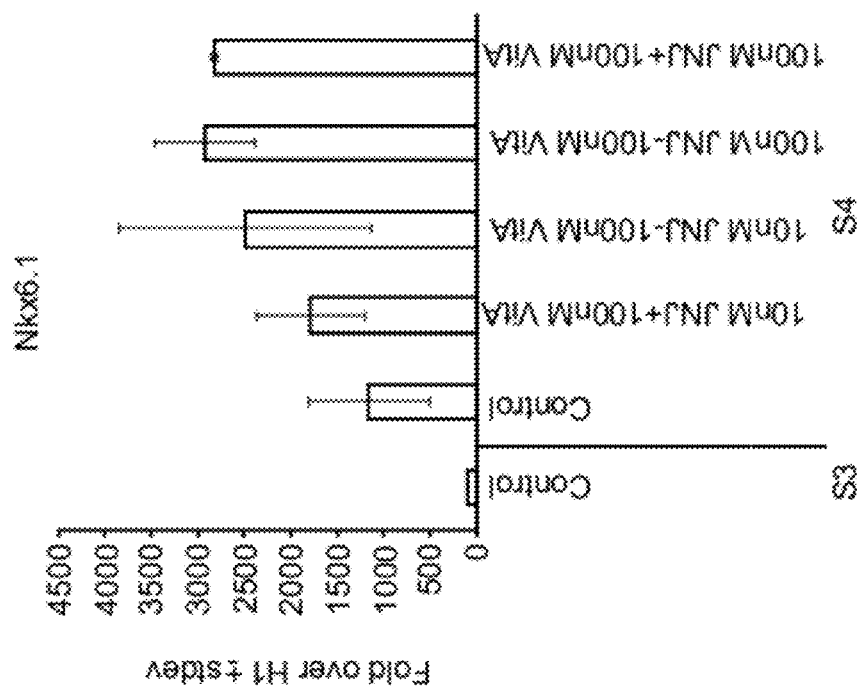
Figure 1H:
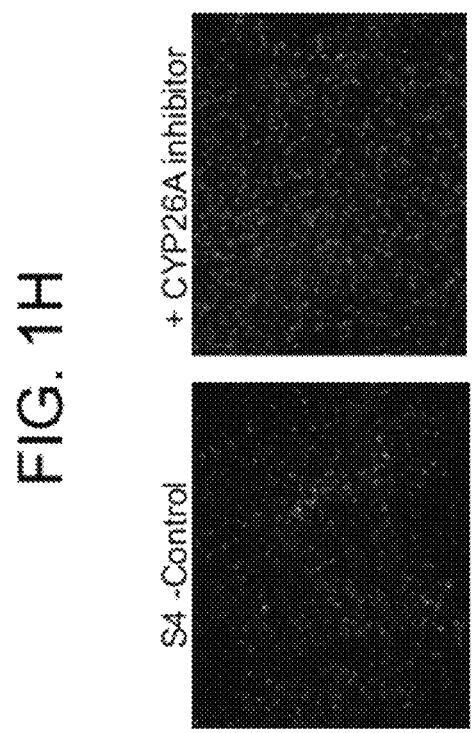
Figure 1G:
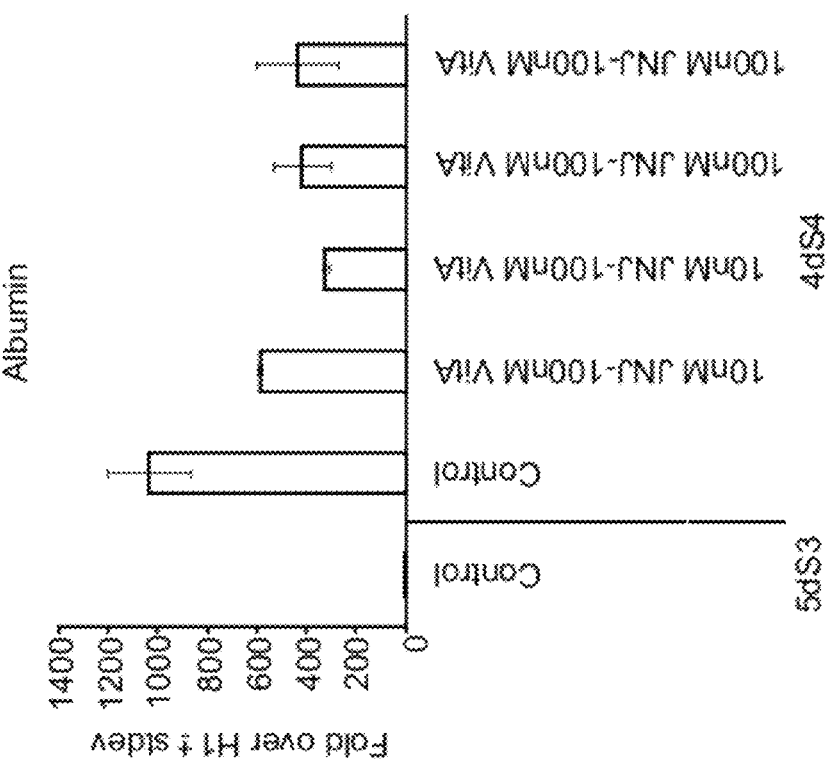

For clarity of disclosure, and not by way of limitation, the detailed description of the invention is divided into the following subsections that describe or illustrate certain features, embodiments or applications of the present invention.

Definitions

Stem cells are undifferentiated cells defined by their ability at the single cell level to both self-renew and differentiate to produce progeny cells, including self-renewing progenitors, non-renewing progenitors, and terminally differentiated cells. Stem cells are also characterized by their ability to differentiate in vitro into functional cells of various cell lineages from multiple germ layers (endoderm, mesoderm and ectoderm), as well as to give rise to tissues of multiple germ layers following transplantation and to contribute substantially to most, if not all, tissues following injection into blastocysts.

Stem cells are classified by their developmental potential as: (1) totipotent, meaning able to give rise to all embryonic and extraembryonic cell types; (2) pluripotent, meaning able to give rise to all embryonic cell types; (3) multipotent, meaning able to give rise to a subset of cell lineages but all within a particular tissue, organ, or physiological system (for example, hematopoietic stem cells (HSC) can produce progeny that include HSC (self-renewal), blood cell restricted oligopotent progenitors, and all cell types and elements (e.g., platelets) that are normal components of the blood); (4) oligopotent, meaning able to give rise to a more restricted subset of cell lineages than multipotent stem cells; and (5) unipotent, meaning able to give rise to a single cell lineage (e.g., spermatogenic stem cells).

Differentiation is the process by which an unspecialized ("uncommitted") or less specialized cell acquires the features of a specialized cell such as, for example, a nerve cell or a muscle cell. A differentiated or differentiation-induced cell is one that has taken on a more specialized ("committed") position within the lineage of a cell. The term "committed", when applied to the process of differentiation, refers to a cell that has proceeded in the differentiation pathway to a point where, under normal circumstances, it will continue to differentiate into a specific cell type or subset of cell types, and cannot, under normal circumstances, differentiate into a different cell type or revert to a less differentiated cell type. De-differentiation refers to the process by which a cell reverts to a less specialized (or committed) position within the lineage of a cell. As used herein, the lineage of a cell defines the heredity of the cell, i.e., which cells it came from and what cells it can give rise to. The lineage of a cell places the cell within a hereditary scheme of development and differentiation. A lineage-specific marker refers to a characteristic specifically associated with the phenotype of cells of a lineage of interest and can be used to assess the differentiation of an uncommitted cell to the lineage of interest.

"Cells expressing markers characteristic of the definitive endoderm lineage", or "Stage 1 cells", or "Stage 1", as used herein, refers to cells expressing at least one of the following markers: SOX17, GATA4, HNF3 beta, GSC, CER1, Nodal, FGF8, Brachyury, Mix-like homeobox protein, FGF4 CD48, eomesodermin (EOMES), DKK4, FGF17, GATA6, CXCR4, C-Kit, CD99, or OTX2. Cells expressing markers characteristic of the definitive endoderm lineage include primitive streak precursor cells, primitive streak cells, mesendoderm cells and definitive endoderm cells.

"Cells expressing markers characteristic of the pancreatic endoderm lineage", as used herein, refers to cells expressing at least one of the following markers: PDX1, NKX6.1, HNF1 beta, PTF1 alpha, HNF6, HNF4 alpha, SOX9, HB9 or PROX1. Cells expressing markers characteristic of the pancreatic endoderm lineage include pancreatic endoderm cells, primitive gut tube cells, and posterior foregut cells.

"Definitive endoderm", as used herein, refers to cells which bear the characteristics of cells arising from the epiblast during gastrulation and which form the gastrointestinal tract and its derivatives. Definitive endoderm cells express the following markers: HNF3 beta, GATA4, SOX17, Cerberus, OTX2, goosecoid, C-Kit, CD99, and MIXL1.

"Markers", as used herein, are nucleic acid or polypeptide molecules that are differentially expressed in a cell of interest. In this context, differential expression means an increased level for a positive marker and a decreased level for a negative marker. The detectable level of the marker nucleic acid or polypeptide is sufficiently higher or lower in the cells of interest compared to other cells, such that the cell of interest can be identified and distinguished from other cells using any of a variety of methods known in the art.

"Pancreatic endocrine precursor cell", as used herein, refers to a cell expressing at least one of the following markers: NGN3, NEUROD, or NKX2.2.

"Posterior foregut cell", as used herein, refers to a cell expressing at least one of the following markers: PDX1 or HNF6.

"Immature pancreatic hormone expressing cells" as used herein, refers to a cell expressing at least one of the following markers: Insulin, glucagon, somatostatin, MAFB, PDX1, ARX, NKX6.1, NKX2.2, or NEUROD.

"Primitive gut tube cell", as used herein, refers to a cell expressing at least one of the following markers: HNF1 beta, or HNF4 alpha.

"Pancreatic endocrine cell", or "Pancreatic hormone expressing cell", or "Cells expressing markers characteristic of the pancreatic endocrine lineage" as used herein, refers to a cell capable of expressing at least one of the following hormones: insulin, glucagon, somatostatin, and pancreatic polypeptide.

Isolation, Expansion and Culture of Pluripotent Stem Cells

Characterization of Pluripotent Stem Cells

Pluripotent stem cells may express one or more of the stage-specific embryonic antigens (SSEA) 3 and 4, and markers detectable using antibodies designated Tra-1-60 and Tra-1-81 (Thomson et al., Science 282:1145, 1998). Differentiation of pluripotent stem cells in vitro results in the loss of SSEA-4, Tra 1-60, and Tra 1-81 expression (if present) and increased expression of SSEA-1. Undifferentiated pluripotent stem cells typically have alkaline phosphatase activity, which can be detected by fixing the cells with 4% paraformaldehyde, and then developing with Vector Red as a substrate, as described by the manufacturer (Vector Laboratories, Burlingame Calif.). Undifferentiated pluripotent stem cells also typically express OCT4 and TERT, as detected by RT-PCR.

Another desirable phenotype of propagated pluripotent stem cells is a potential to differentiate into cells of all three germinal layers: endoderm, mesoderm, and ectoderm tissues. Pluripotency of pluripotent stem cells can be confirmed, for example, by injecting cells into severe combined immunodeficient (SCID) mice, fixing the teratomas that form using 4% paraformaldehyde, and then examining them histologically for evidence of cell types from the three germ layers. Alternatively, pluripotency may be determined by the creation of embryoid bodies and assessing the embryoid bodies for the presence of markers associated with the three germinal layers.

Propagated pluripotent stem cell lines may be karyotyped using a standard G-banding technique and compared to published karyotypes of the corresponding primate species. It is desirable to obtain cells that have a "normal karyotype," which means that the cells are euploid, wherein all human chromosomes are present and not noticeably altered.

Sources of Pluripotent Stem Cells

The types of pluripotent stem cells that may be used include established lines of pluripotent cells derived from tissue formed after gestation, including pre-embryonic tissue (such as, for example, a blastocyst), embryonic tissue, or fetal tissue taken any time during gestation, typically but not necessarily before approximately 10 to 12 weeks gestation. Non-limiting examples are established lines of human embryonic stem cells or human embryonic germ cells, such as, for example the human embryonic stem cell lines H1, H7, and H9 (WiCell). Also contemplated is use of the compositions of this disclosure during the initial establishment or stabilization of such cells, in which case the source cells would be primary pluripotent cells taken directly from the source tissues. Also suitable are cells taken from a pluripotent stem cell population already cultured in the absence of feeder cells. Also suitable are mutant human embryonic stem cell lines, such as, for example, BG01v (BresaGen, Athens, Ga.).

In one embodiment, human embryonic stem cells are prepared as described by Thomson et al. (U.S. Pat. No. 5,843,780; Science 282:1145, 1998; Curr. Top. Dev. Biol. 38:133 ff., 1998; Proc. Natl. Acad. Sci. U.S.A. 92:7844, 1995).

Culture of Pluripotent Stem Cells

In one embodiment, pluripotent stem cells are cultured on a layer of feeder cells that support the pluripotent stem cells in various ways. Alternatively, pluripotent stem cells are cultured in a culture system that is essentially free of feeder cells, but nonetheless supports proliferation of pluripotent stem cells without undergoing substantial differentiation. The growth of pluripotent stem cells in feeder-free culture without differentiation is supported using a medium conditioned by culturing previously with another cell type. Alternatively, the growth of pluripotent stem cells in feeder-free culture without differentiation is supported using a chemically defined medium.

In one embodiment, pluripotent stem cells may be cultured on a mouse embryonic fibroblast feeder cell layer according to the methods disclosed in Reubinoff et al (Nature Biotechnology 18: 399-404 (2000)). Alternatively, pluripotent stem cells may be cultured on a mouse embryonic fibroblast feeder cell layer according to the methods disclosed in Thompson et al (Science 6 Nov. 1998: Vol. 282. no. 5391, pp. 1145-1147). Alternatively, pluripotent stem cells may be cultured on any one of the feeder cell layers disclosed in Richards et al, (Stem Cells 21: 546-556, 2003).

In one embodiment, pluripotent stem cells may be cultured on a human feeder cell layer according to the methods disclosed in Wang et al (Stem Cells 23: 1221-1227, 2005). In an alternate embodiment, pluripotent stem cells may be cultured on the human feeder cell layer disclosed in Stojkovic et al (Stem Cells 2005 23: 306-314, 2005). Alternatively, pluripotent stem cells may be cultured on the human feeder cell layer disclosed in Miyamoto et al (Stem Cells 22: 433-440, 2004). Alternatively, pluripotent stem cells may be cultured on the human feeder cell layer disclosed in Amit et al (Biol. Reprod 68: 2150-2156, 2003). Alternatively, pluripotent stem cells may be cultured on the human feeder cell layer disclosed in Inzunza et al (Stem Cells 23: 544-549, 2005).

In one embodiment, pluripotent stem cells may be cultured in culture media derived according to the methods disclosed in US20020072117. Alternatively, pluripotent stem cells may be cultured in culture media derived according to the methods disclosed in U.S. Pat. No. 6,642,048. Alternatively, pluripotent stem cells may be cultured in culture media derived according to the methods disclosed in WO2005014799. Alternatively, pluripotent stem cells may be cultured in culture media derived according to the methods disclosed in Xu et al (Stem Cells 22: 972-980, 2004). Alternatively, pluripotent stem cells may be cultured in culture media derived according to the methods disclosed in US20070010011. Alternatively, pluripotent stem cells may be cultured in culture media derived according to the methods disclosed in US20050233446. Alternatively, pluripotent stem cells may be cultured in culture media derived according to the methods disclosed in U.S. Pat. No. 6,800,480. Alternatively, pluripotent stem cells may be cultured in culture media derived according to the methods disclosed in WO2005065354.

In one embodiment, pluripotent stem cells may be cultured according to the methods disclosed in Cheon et al (BioReprod DOI:10.1095/biolreprod.105.046870, Oct. 19, 2005). Alternatively, pluripotent stem cells may be cultured according to the methods disclosed in Levenstein et al (Stem Cells 24: 568-574, 2006). Alternatively, pluripotent stem cells may be cultured according to the methods disclosed in US20050148070. Alternatively, pluripotent stem cells may be cultured according to the methods disclosed in US20050244962. Alternatively, pluripotent stem cells may be cultured according to the methods disclosed in WO2005086845.

The pluripotent stem cells may be plated onto a suitable culture substrate. In one embodiment, the suitable culture substrate is an extracellular matrix component, such as, for example, those derived from basement membrane or that may form part of adhesion molecule receptor-ligand couplings. In one embodiment, the suitable culture substrate is MATRIGEL® (Becton Dickenson). MATRIGEL® is a soluble preparation from Engelbreth-Holm Swarm tumor cells that gels at room temperature to form a reconstituted basement membrane.

Other extracellular matrix components and component mixtures are suitable as an alternative. Depending on the cell type being proliferated, this may include laminin, fibronectin, proteoglycan, entactin, heparan sulfate, and the like, alone or in various combinations.

The pluripotent stem cells may be plated onto the substrate in a suitable distribution and in the presence of a medium that promotes cell survival, propagation, and retention of the desirable characteristics. All these characteristics benefit from careful attention to the seeding distribution and can readily be determined by one of skill in the art.

Suitable culture media may be made from the following components, such as, for example, Dulbecco's modified Eagle's medium (DMEM), Gibco #11965-092; Knockout Dulbecco's modified Eagle's medium (KO DMEM), Gibco #10829-018; Ham's F12/50% DMEM basal medium; 200 mM L-glutamine, Gibco #15039-027; non-essential amino acid solution, Gibco 11140-050; β-mercaptoethanol, Sigma # M7522; human recombinant basic fibroblast growth factor (bFGF), Gibco #13256-029.

Formation of Pancreatic Endocrine Precursor Cells from Pluripotent Stem Cells

The present invention provides methods for the formation of a population of pancreatic precursor cells from a population of pluripotent stem cells. In one embodiment, the present invention provides methods to further differentiate the pancreatic endocrine precursor cells into cells expressing markers of the pancreatic endocrine lineage.

In one embodiment, the present invention provides a method for producing of pancreatic precursor cells, comprising the steps of:
  a. Culturing a population of pluripotent stem cells,
  b. Differentiating the population of pluripotent stem cells into a population of cells expressing markers characteristic of the definitive endoderm lineage;
  c. Differentiating the population of cells expressing markers characteristic of the definitive endoderm lineage into a population of primitive gut tube cells;
  d. Differentiating the population of primitive gut tube cells into a population of posterior foregut cells; and
  e. Differentiating the population of posterior foregut cells into a population of pancreatic endocrine precursor cells by treating the population of posterior foregut cells with a medium supplemented with a CYP26A inhibitor.

The population of pancreatic endocrine precursor cells may be further treated to form a population of cells expressing markers characteristic of the pancreatic endocrine lineage.

The efficiency of differentiation may be determined by exposing a treated cell population to an agent (such as an antibody) that specifically recognizes a protein marker expressed by cells expressing markers characteristic of the desired cell type.

Methods for assessing expression of protein and nucleic acid markers in cultured or isolated cells are standard in the art. These include quantitative reverse transcriptase polymerase chain reaction (RT-PCR), Northern blots, in situ hybridization (see, e.g., Current Protocols in Molecular Biology (Ausubel et al., eds. 2001 supplement)), and immunoassays such as immunohistochemical analysis of sectioned material, Western blotting, and for markers that are accessible in intact cells, flow cytometry analysis (FACS) (see, e.g., Harlow and Lane, Using Antibodies: A Laboratory Manual, New York: Cold Spring Harbor Laboratory Press (1998)).

Characteristics of pluripotent stem cells are well known to those skilled in the art, and additional characteristics of pluripotent stem cells continue to be identified. Pluripotent stem cell markers include, for example, the expression of one or more of the following: ABCG2, cripto, FOXD3, CONNEXIN43, CONNEXIN45, OCT4, SOX2, NANOG, hTERT, UTF1, ZFP42, SSEA-3, SSEA-4, Tra 1-60, Tra 1-81.

After treating pluripotent stem cells with the methods of the present invention, the differentiated cells may be purified by exposing a treated cell population to an agent (such as an antibody) that specifically recognizes a protein marker, such as CXCR4, expressed by cells expressing markers characteristic of the definitive endoderm lineage.

Pluripotent stem cells suitable for use in the present invention include, for example, the human embryonic stem cell line H9 (NIH code: WA09), the human embryonic stem cell line H1 (NIH code: WA01), the human embryonic stem cell line H7 (NIH code: WA07), and the human embryonic stem cell line SA002 (Cellartis, Sweden). Also suitable for use in the present invention are cells that express at least one of the following markers characteristic of pluripotent cells: ABCG2, cripto, CD9, FOXD3, CONNEXIN43, CONNEXIN45, OCT4, SOX2, NANOG, hTERT, UTF1, ZFP42, SSEA-3, SSEA-4, Tra 1-60, and Tra 1-81.

Markers characteristic of the definitive endoderm lineage are selected from the group consisting of SOX17, GATA4, HNF3 beta, GSC, CER1, Nodal, FGF8, Brachyury, Mix-like homeobox protein, FGF4, CD48, eomesodermin (EOMES), DKK4, FGF17, GATA6, CXCR4, C-Kit, CD99, and OTX2. Suitable for use in the present invention is a cell that expresses at least one of the markers characteristic of the definitive endoderm lineage. In one aspect of the present invention, a cell expressing markers characteristic of the definitive endoderm lineage is a primitive streak precursor cell. In an alternate aspect, a cell expressing markers characteristic of the definitive endoderm lineage is a mesendoderm cell. In an alternate aspect, a cell expressing markers characteristic of the definitive endoderm lineage is a definitive endoderm cell.

Markers characteristic of the pancreatic endoderm lineage (which includes primitive gut tube cells and posterior foregut cells) are selected from the group consisting of PDX1, NKX6.1, HNF1 beta, PTF1 alpha, HNF6, HNF4 alpha, SOX9, HB9 and PROX1. Suitable for use in the present invention is a cell that expresses at least one of the markers characteristic of the pancreatic endoderm lineage. In one aspect of the present invention, a cell expressing markers characteristic of the pancreatic endoderm lineage is a pancreatic endoderm cell.

Markers characteristic of the pancreatic endocrine lineage are selected from the group consisting of NGN3, NEUROD, ISL1, PDX1, NKX6.1, PAX4, NGN3, and PTF-1 alpha. In one embodiment, a pancreatic endocrine cell is capable of expressing at least one of the following hormones: insulin, glucagon, somatostatin, and pancreatic polypeptide. Suitable for use in the present invention is a cell that expresses at least one of the markers characteristic of the pancreatic endocrine lineage. In one aspect of the present invention, a cell expressing markers characteristic of the pancreatic endocrine lineage is a pancreatic endocrine cell. The pancreatic endocrine cell may be a pancreatic hormone-expressing cell. Alternatively, the pancreatic endocrine cell may be a pancreatic hormone-secreting cell.

In one aspect of the present invention, the pancreatic endocrine cell is a cell expressing markers characteristic of the β cell lineage. A cell expressing markers characteristic of the β cell lineage expresses PDX1 and at least one of the following transcription factors: NGN3, NKX2.2, NKX6.1, NEUROD, ISL1, HNF3 beta, MAFA, PAX4, and PAX6. In one aspect of the present invention, a cell expressing markers characteristic of the β cell lineage is a β cell.

Formation of Cells Expressing Markers
Characteristic of the Definitive Endoderm Lineage
from Pluripotent Stem Cells Populations of cells expressing markers characteristic of the definitive endoderm lineage may be formed from populations of pluripotent stem cells by any method in the art.

For example, populations of pluripotent stem cells may be differentiated into cells expressing markers characteristic of the definitive endoderm lineage according to the methods disclosed in D'Amour et al, Nature Biotechnology 23, 1534-1541 (2005).

For example, populations of pluripotent stem cells may be differentiated into cells expressing markers characteristic of the definitive endoderm lineage according to the methods disclosed in Shinozaki et al, Development 131, 1651-1662 (2004).

For example, populations of pluripotent stem cells may be differentiated into cells expressing markers characteristic of the definitive endoderm lineage according to the methods disclosed in McLean et al, Stem Cells 25, 29-38 (2007).

For example, populations of pluripotent stem cells may be differentiated into cells expressing markers characteristic of the definitive endoderm lineage according to the methods disclosed in D'Amour et al, Nature Biotechnology 24, 1392-1401 (2006).

For example, populations of pluripotent stem cells may be differentiated into cells expressing markers characteristic of the definitive endoderm lineage according to the methods disclosed in U.S. patent application Ser. No. 11/736,908.

For example, populations of pluripotent stem cells may be differentiated into cells expressing markers characteristic of the definitive endoderm lineage according to the methods disclosed in U.S. patent application Ser. No. 11/779,311.

For example, populations of pluripotent stem cells may be differentiated into cells expressing markers characteristic of the definitive endoderm lineage according to the methods disclosed in U.S. patent application Ser. No. 12/493,741.

For example, populations of pluripotent stem cells may be differentiated into cells expressing markers characteristic of the definitive endoderm lineage according to the methods disclosed in U.S. patent application Ser. No. 12/494,789.

Formation of Cells Expressing Markers
Characteristic of the Pancreatic Endoderm Lineage Cells expressing markers characteristic of the pancreatic endoderm lineage include pancreatic endoderm cells, primitive gut tube cells, and posterior foregut cells. In one embodiment, populations of cells expressing markers characteristic of the definitive endoderm lineage formed by the methods of the present invention are further differentiated into populations of cells expressing markers characteristic of the pancreatic endoderm lineage by any method in the art.

For example, populations of cells expressing markers characteristic of the definitive endoderm lineage obtained according to the methods of the present invention may be further differentiated into populations of cells expressing markers characteristic of the pancreatic endoderm lineage by treating the population of cells expressing markers characteristic of the definitive endoderm lineage according to the methods disclosed in D'Amour et al, Nature Biotechnology 24, 1392-1401 (2006).

For example, populations of cells expressing markers characteristic of the definitive endoderm lineage obtained according to the methods of the present invention may be further differentiated into populations of cells expressing markers characteristic of the pancreatic endoderm lineage by treating the population of cells expressing markers characteristic of the definitive endoderm lineage according to the methods disclosed in U.S. patent application Ser. No. 11/736,908.

Formation of a Population of Pancreatic Endocrine
Precursor Cells

In one embodiment, the present invention provides a method for producing of pancreatic precursor cells, comprising the steps of:
 a. Culturing a population of pluripotent stem cells,
 b. Differentiating the population of pluripotent stem cells into a population of cells expressing markers characteristic of the definitive endoderm lineage;

c. Differentiating the population of cells expressing markers characteristic of the definitive endoderm lineage into a population of primitive gut tube cells;
d. Differentiating the population of primitive gut tube cells into a population of posterior foregut cells; and
e. Differentiating the population of posterior foregut cells into a population of pancreatic endocrine precursor cells by treating the population of posterior foregut cells with a medium supplemented with a CYP26A inhibitor.

The CYP26A inhibitor may be used at a concentration from about 1 nM to about 1000 nM. Alternatively, the CYP26A inhibitor may be used at a concentration from about 10 nM to about 100 nM.

Any CYP26A inhibitor is suitable for use in the present invention. For example, the CYP26A inhibitor may be selected from the compounds disclosed in U.S. Pat. No. 7,468,391. Alternatively, the CYP26A inhibitor may be selected from the compounds disclosed in US Patent Application No. 2005/0187298A1. Alternatively, the CYP26A inhibitor may be selected from the compounds disclosed in US Patent Application No. 2004/0106216A1. Alternatively, the CYP26A inhibitor may be selected from the compounds disclosed in WO2005058301A1. Alternatively, the CYP26A inhibitor may be selected from the compounds disclosed in PNAS May 12, 2009 vol. 106 no. 19 7864-7869. In one embodiment, the CYP26A inhibitor is N-{4-[2-Ethyl-1-(1H-1,2,4-triazol-1-yl)butyl]phenyl}-1,3-benzothiazol-2-amine. See Formula 1.

Formula 1

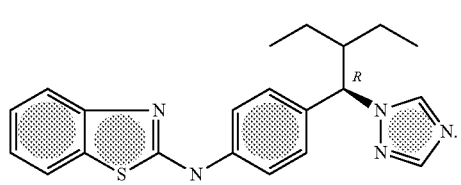

In one embodiment, the medium supplemented with a CYP26A inhibitor is further supplemented with at least one factor selected from the group consisting of a factor capable of inhibiting BMP, a TGFβ receptor signaling inhibitor, vitamin A and a PKC activator.

In one embodiment, the factor capable of inhibiting BMP is noggin. Noggin may be used at a concentration from about 50 ng/ml to about 500 μg/ml. In one embodiment, noggin is used at a concentration of 100 ng/ml.

In one embodiment, the TGFβ receptor signaling inhibitor is an inhibitor of ALK5. In one embodiment, the inhibitor of ALK5 is ALK5 inhibitor II. The ALK5 inhibitor II may be used at a concentration from about 0.1 μM to about 10 μM. In one embodiment, ALK5 inhibitor II is used at a concentration of 1 μM.

In one embodiment, the PKC activator is selected from the group consisting of (2S,5S)-(E,E)-8-(5-(4-(Trifluoromethyl)phenyl)-2,4-pentadiemoylamino)benzolactam, Indolactam V (ILV), phorbol-12-myristate-13-acetate (PMA), and phorbol-12,13-dibutyrate (PDBu). In one embodiment, the protein kinase C activator is (2S,5S)-(E,E)-8-(5-(4-(Trifluoromethyl)phenyl)-2,4-pentadiemoylamino)benzolactam. (2S,5S)-(E,E)-8-(5-(4-(Trifluoromethyl)phenyl)-2,4-pentadiemoylamino)benzolactam may be used at a concentration from about 20 nM to about 500 nM. (2S,5S)-(E,E)-8-(5-(4-(Trifluoromethyl)phenyl)-2,4-pentadiemoylamino)benzolactam, is referred to herein as "TPB".

Formation of Cells Expressing Markers Characteristic of the Pancreatic Endocrine Lineage In one embodiment, the populations of pancreatic endocrine precursor cells produced by the methods of the present invention are further differentiated into populations of cells expressing markers characteristic of the pancreatic endocrine lineage by any method in the art.

For example, populations of cells expressing markers characteristic of the pancreatic endoderm lineage may be further differentiated into populations of cells expressing markers characteristic of the pancreatic endocrine lineage, by treating the population of cells expressing markers characteristic of the pancreatic endoderm lineage according to the methods disclosed in D'Amour et al, Nature Biotechnology, 2006.

For example, populations of cells expressing markers characteristic of the pancreatic endoderm lineage may be further differentiated into populations of cells expressing markers characteristic of the pancreatic endocrine lineage, by treating the population of cells expressing markers characteristic of the pancreatic endoderm lineage according to the methods disclosed in D'Amour et al, Nature Biotechnology, 2006.

For example, populations of cells expressing markers characteristic of the pancreatic endoderm lineage may be further differentiated into populations of cells expressing markers characteristic of the pancreatic endocrine lineage, by treating the population of cells expressing markers characteristic of the pancreatic endoderm lineage according to the methods disclosed in U.S. patent application Ser. No. 11/736,908.

For example, populations of cells expressing markers characteristic of the pancreatic endoderm lineage may be further differentiated into populations of cells expressing markers characteristic of the pancreatic endocrine lineage, by treating the population of cells expressing markers characteristic of the pancreatic endoderm lineage according to the methods disclosed in U.S. patent application Ser. No. 11/779,311.

For example, populations of cells expressing markers characteristic of the pancreatic endoderm lineage may be further differentiated into populations of cells expressing markers characteristic of the pancreatic endocrine lineage, by treating the population of cells expressing markers characteristic of the pancreatic endoderm lineage according to the methods disclosed in U.S. patent application Ser. No. 60/953,178.

For example, populations of cells expressing markers characteristic of the pancreatic endoderm lineage may be further differentiated into populations of cells expressing markers characteristic of the pancreatic endocrine lineage, by treating the population of cells expressing markers characteristic of the pancreatic endoderm lineage according to the methods disclosed in U.S. patent application Ser. No. 60/990,529.

The present invention is further illustrated, but not limited by, the following examples.

EXAMPLES

Example 1

Differentiation of Cells of the Human Embryonic Stem Cell Line H1 into Pancreatic Endocrine Precursor Cells in Cell Culture Medium Lacking FBS and Containing an Inhibitor of CYP26A Cells of the human embryonic stem cells line H1 (p40-p50) were cultured on MATRIGEL®-coated dishes (1:30 dilution) (BD Biosciences; Cat #356231) in MEF-CM (mouse embryonic fibroblast conditioned medium) as colonies and differentiated into pancreatic endocrine precursor cells as follows:

a. Stage I (Definitive Endoderm): Human embryonic stem cells were cultured in RPMI medium supplemented with 2% fatty acid-free BSA (Catalog#68700, Proliant, IA), and 100 ng/ml activin A (R&D Systems, MN) plus 20 ng/ml WNT-3a (Catalog#1324-WN-002, R&D Systems, MN) plus 8 ng/ml of bFGF (Catalog#100-18B, PeproTech, NJ), for one day, followed by treatment with RPMI medium supplemented with 2% BSA and 100 ng/ml activin A plus 8 ng/ml of bFGF for an additional two days, then b. Stage II (Primitive gut tube): Cells were treated with RPMI+2% fatty acid-free BSA and 50 ng/ml FGF7, for two days, then c. Stage III (Posterior foregut): Cells were treated with DMEM/High-Glucose supplemented with 1:200 dilution of ITS-X (Invitrogen, CA) and 0.1% BSA (Lipid Rich) (Invitrogen, Ca No. 11021-045), 50 ng/ml FGF7, 0.25 µM SANT-1, 2 µM Retinoic acid (RA) (Sigma, MO), 100 ng/ml of Noggin (R & D Systems, MN), 2.5 µM 4-[4-(4-Fluorophenyl)-1-(3-phenylpropyl)-5-pyridin-4-yl-1H-imidazol-2-yl]but-3-yn-1-ol (a P38 inhibitor disclosed in U.S. Pat. No. 6,521,655), and activin A at 20 ng/ml for five days, then d. Stage IV (Pancreatic endocrine precursor): Cells were treated with DMEM/High-Glucose supplemented with 1:200 dilution of ITS-X (Invitrogen, CA) and 0.1% BSA (Invitrogen, CA), 100 ng/ml Noggin, 1 µM ALK5 inhibitor (SD-208, disclosed in Molecular Pharmacology 2007 72:152-161), 500 nM TPB (α-Amyloid Precursor Protein Modulator) (Catalogue #565740, EMD, CA), and 10-100 nM of the CYP26A inhibitor N-{4-[2-Ethyl-1-(1H-1,2,4-triazol-1-yl)butyl]phenyl}-1,3-benzothiazol-2-amine, and 10-100 nM Vitamin A (Catalogue# R7632, Sigma, MO) for four days, or In some of the cultures, the Stage IV was extended to six days. mRNA was isolated at stages III and IV for real-time PCR analysis of pancreatic related genes. As shown in FIG. 1, addition of the CYP26A inhibitor at stage IV significantly boosted expression of endocrine precursor markers (NGN3, Pax4, NeuroD) along with the pancreatic endoderm marker NKX6.1 in a dose dependent manner. Addition of vitamin A along with the CYP26A inhibitor did not significantly modify expression of pancreatic endoderm or endocrine precursor markers. Furthermore, addition of the CYP26A inhibitor at stage IV decreased expression of CDX2 (an intestinal marker) and albumin (a liver marker) Immunostaining for NGN3 (Catalogue# AF3444, R & D systems, MN) at stage IV clearly showed a significant boost in expression of NGN3 for cultures treated with 100 nM of the CYP26A inhibitor.

Example 2

Figure 2B:
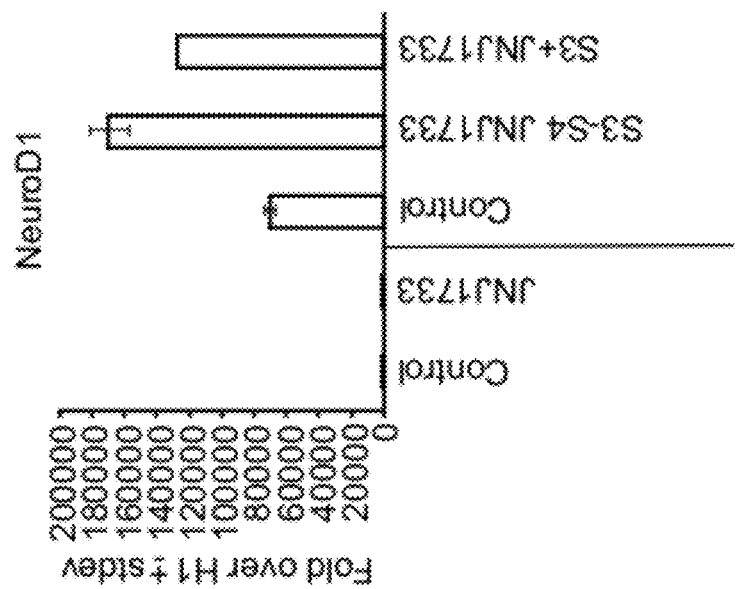
FIG. 2 shows real-time PCR data obtained from samples obtained from cells at stages III-IV, of the protocol outlined in Example 2, for a) NGN3, b) NEUROD, c) CDX2, d) NKX6.1 and, e) PDX1. The y-axis is fold expression over undifferentiated H1 cells.
Figure 2A:
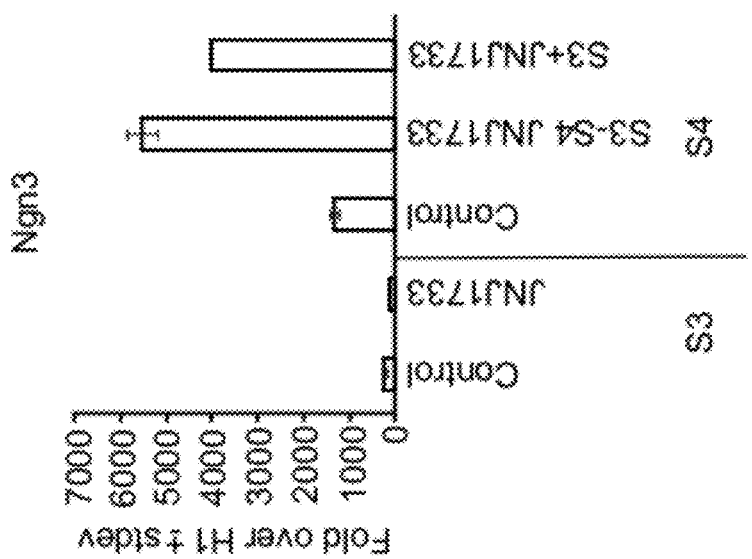

An Alternative Method for the Differentiation of Cells of the Human Embryonic Stem Cell Line H1 into Pancreatic Endocrine Precursor Cells in Cell Culture Medium Lacking FBS and Containing an Inhibitor of CYP26A Cells of the human embryonic stem cells line H1 (p40-p52) were seeded as single cells at a density of 100000 cells/cm$^2$ on MATRIGEL®-coated dishes (1:30 dilution) (BD Biosciences; Cat #356231) in MEF-CM (mouse embryonic fibroblast conditioned media supplemented with 16 ng/ml of FGF2 (Catalog#100-18B, PeproTech, NJ) and 10 µM of Y27632 (Rock inhibitor, Catalogue# Y0503, Sigma, MO). 72 hrs post seeding, cultures were differentiated into definitive endoderm (DE) as follows:

a. Stage I (Definitive Endoderm): Human embryonic stem cells were treated with MCDB-131 (Catalogue#10372-019, Invitrogen, CA) medium supplemented with 2% fatty acid-free BSA (Catalog#68700, Proliant, IA), 0.0025 g/ml sodium bicarbonate (Catalogue # S3187, Sigma, MO), 1X GlutaMax™ (Catalogue #35050-079, Invitrogen, Ca) and 100 ng/ml activin A (R&D Systems, MN) plus 20 ng/ml WNT-3a (Catalog#1324-WN-002, R&D Systems, MN) for one day, followed by treatment with MCDB-131 medium supplemented with 2% BSA, sodium bicarbonate, Glutamax, and 100 ng/ml activin A for an additional three days, then b. Stage II (Primitive gut tube): Cells were treated with MCDB-131+2% fatty acid-free BSA and 50 ng/ml FGF7 and for three days, then c. Stage III (Posterior foregut): Cells were treated with MCDB-131/High-Glucose (25 mM glucose) supplemented with 1:200 dilution of ITS-X (Invitrogen, CA), 1X GlutaMax™ (Catalogue #35050-079, Invitrogen, Ca), 0.0025 g/ml sodium bicarbonate (Catalogue # S3187, Sigma, MO), 0.1% BSA (Lipid Rich) (Invitrogen, Ca No. 11021-045), 50 ng/ml FGF7, 0.25 µM SANT-1, 2 µM Retinoic acid (RA) (Sigma, MO), 2.5 µM 4-[4-(4-Fluorophenyl)-1-(3-phenylpropyl)-5-pyridin-4-yl-1H-imidazol-2-yl]but-3-yn-1-ol (a p38 inhibitor, disclosed in U.S. Pat. No. 6,521,655), 100 nM LDN-193189 (BMP receptor inhibitor, Catalogue #04-0019, Stemgent, CA), 500 nM of the CYP26A inhibitor N-{4-[2-Ethyl-1-(1H-1,2,4-triazol-1-yl)butyl]phenyl}-1,3-benzothiazol-2-amine, and activin A at 20 ng/ml for four days, then d. Stage IV (Pancreatic endocrine precursor): Cells were treated MCDB-131/High-Glucose (25 mM glucose) supplemented with 1:200 dilution of ITS-X (Invitrogen, CA) and 0.1% BSA (Invitrogen, Ca), 1X GlutaMax™ (Catalogue #35050-079, Invitrogen, Ca), 0.0025 g/ml sodium bicarbonate (Catalogue # S3187, Sigma, MO), 1 µM ALK5 inhibitor (SD-208, disclosed in Molecular Pharmacology 2007 72:152-161), 500 nM PDBu (PKC activator) (Catalogue #P1269, Sigma, MO), 100 nM LDN-193189 (BMP receptor inhibitor, Catalogue #04-0019, Stemgent, CA), 0.25 µM SANT-1 (#S4572, Sigma, MO), and 500 nM of the CYP26A inhibitor N-{4-[2-Ethyl-1-(1H-1,2,4-triazol-1-yl)butyl]phenyl}-1,3-benzothiazol-2-amine for seven days, or e. Stage IV (Pancreatic endocrine precursor): Cells were treated MCDB-131/High-Glucose (25 mM glucose) supplemented with 1:200 dilution of ITS-X (Invitrogen, CA) and 0.1% BSA (Invitrogen, Ca), 1X GlutaMax™ (Catalogue #35050-079, Invitrogen, Ca), 0.0025 g/ml sodium bicarbonate (Catalogue # S3187, Sigma, MO), 1 µM ALK5 inhibitor (SD-208, disclosed in Molecular Pharmacology 2007 72:152-161), 500 nM PDBu (PKC activator) (Catalogue #P1269, Sigma, MO), 100 nM LDN-193189 (BMP receptor inhibitor, Catalogue #04-0019, Stemgent, CA), 0.25 µM SANT-1 (#S4572, Sigma, MO) for seven days.

mRNA was isolated at stages III and IV for real-time PCR analysis of pancreatic related genes. Similar to the results observed in Example 1 above, addition of CYP26A inhibitor to stage IV enhanced expression of pancreatic endocrine precursor markers, such as NGN3 and NeuroD. (See FIG. 2). Addition of the inhibitor to both stages III and IV further enhanced expression of NGN3 and NeuroD. Surprisingly, addition of the CYP26A inhibitor to stage III (in the presence of retinoic acid) significantly down regulated PDX-1 and NKX6.1, while enhancing expression of CDX2. These results suggest that the optimal stage for addition of CYP26A inhibitor is stage IV.

Example 3

An Alternative Method for the Differentiation of Cells of the Human Embryonic Stem Cell Line H1 into Pancreatic Endocrine Cells in Cell Culture Medium Lacking FBS and Containing an Inhibitor of CYP26A Cells of the human embryonic stem cells line H1 (p40-p52) were seeded as single cells at a density of 100000 cells/cm² on MATRIGEL®-coated dishes (1:30 dilution) (BD Biosciences; Cat #356231) in MEF-CM (mouse embryonic fibroblast conditioned media supplemented) with 16 ng/ml of FGF2 (Catalog#100-18B, PeproTech, NJ) and 10 µM of Y27632 (Rock inhibitor, Catalogue#Y0503, Sigma, MO). 72 hrs post seeding, cultures were differentiated into definitive endoderm (DE) as follows:

- a. Stage I (Definitive Endoderm): Human embryonic stem cells cultured as single cells on Matrigel-coated dishes were treated with MCDB-131 (Catalogue#10372-019, Invitrogen, CA) medium supplemented with 2% fatty acid-free BSA (Catalog#68700, Proliant, IA), 0.0025 g/ml sodium bicarbonate (Catalogue # S3187, Sigma, MO), 1X GlutaMax™ (Catalogue #35050-079, Invitrogen, Ca) and 100 ng/ml GDF-8 (R&D Systems, MN) plus 2.5 µM of the GSK3B inhibitor 14-Prop-2-en-1-yl-3,5,7,14,17,23,27-heptaazatetracyclo[19.3.1.1~2,6~0.1~8,12~]heptacosa-1(25),2(27),3,5,8(26),9,11,21,23-nonaen-16-one for one day, followed by treatment with MCDB-131 medium supplemented with 2% BSA, sodium bicarbonate, Glutamax, and 100 ng/ml GDF-8 for an additional three days, then
- b. Stage II (Primitive gut tube): Cells were treated with MCDB-131+2% fatty acid-free BSA and 50 ng/ml FGF7 and for two days, then
- c. Stage III (Posterior foregut): Cells were treated with MCDB131/High-Glucose (25 mM glucose) supplemented with 1:200 dilution of ITS-X (Invitrogen, CA), 1X GlutaMax™ (Catalogue #35050-079, Invitrogen, Ca), 0.0025 g/ml sodium bicarbonate (Catalogue # S3187, Sigma, MO), 0.1% BSA (Lipid Rich) (Invitrogen, Ca No. 11021-045), 50 ng/ml FGF7, 0.25 µM SANT-1, 2 µM Retinoic acid (RA) (Sigma, MO), 2.5 µM 4-[4-(4-Fluorophenyl)-1-(3-phenylpropyl)-5-pyridin-4-yl-1H-imidazol-2-yl]but-3-yn-1-ol, 100 nM LDN-193189 (BMP receptor inhibitor, Catalogue #04-0019, Stemgent, CA), and activin A at 20 ng/ml for four days, then
- d. Stage IV (Pancreatic precursor): Cells were treated MCDB131/High-Glucose (25 mM glucose) supplemented with 1:200 dilution of ITS-X (Invitrogen, CA) and 0.1% BSA (Invitrogen, Ca), 1X GlutaMax™ (Catalogue #35050-079, Invitrogen, Ca), 0.0025 g/ml sodium bicarbonate (Catalogue # S3187, Sigma, MO), 100 nM LDN-193189 (BMP receptor inhibitor, Catalogue #04-0019, Stemgent, CA), 50 nM PDBu (PKC activator) (Catalogue #P1269, Sigma, MO), 0.25 µM SANT-1 (#S4572, Sigma, MO), and 100 nM of the CYP26A inhibitor N-{4-[2-Ethyl-1-(1H-1,2,4-triazol-1-yl)butyl]phenyl}-1,3-benzothiazol-2-amine for three days, then
- e. Stage V (Pancreatic endocrine precursor): Cells were treated MCDB131/High-Glucose (25 mM glucose) supplemented with 1:200 dilution of ITS-X (Invitrogen, CA) and 0.1% BSA (Invitrogen, Ca), 1X GlutaMax™ (Catalogue #35050-079, Invitrogen, Ca), 0.0025 g/ml sodium bicarbonate (Catalogue # S3187, Sigma, MO), 100 nM LDN-193189 (BMP receptor inhibitor, Catalogue #04-0019, Stemgent, CA), 0.25 µM SANT-1 (#S4572, Sigma, MO), 2 µM ALK5 inhibitor (SD-208, disclosed in Molecular Pharmacology 2007 72:152-161) and 100 nM of the CYP26A inhibitor N-{4-[2-Ethyl-1-(1H-1,2,4-triazol-1-yl)butyl]phenyl}-1,3-benzothiazol-2-amine for three days, then
- f. Stage VI (Immature pancreatic hormone expressing cells): Cells were treated MCDB131/High-Glucose (25 mM glucose) supplemented with 1:200 dilution of ITS-X (Invitrogen, CA) and 0.1% BSA (Invitrogen, Ca), 1X GlutaMax™ (Catalogue #35050-079, Invitrogen, Ca), 0.0025 g/ml sodium bicarbonate (Catalogue # S3187, Sigma, MO), 100 nM LDN-193189 (BMP receptor inhibitor, Catalogue #04-0019, Stemgent, CA), and 2 µM ALK5 inhibitor (SD-208, disclosed in Molecular Pharmacology 2007 72:152-161) for three days, then
- g. Stage VII (Pancreatic hormone expressing cells): Cells were treated MCDB131/High-Glucose (25 mM glucose) supplemented with 1:200 dilution of ITS-X (Invitrogen, CA) and 0.1% BSA (Invitrogen, Ca), 1X GlutaMax™ (Catalogue #35050-079, Invitrogen, Ca), 0.0025 g/ml sodium bicarbonate (Catalogue # S3187, Sigma, MO), 100 nM LDN-193189 (BMP receptor inhibitor, Catalogue #04-0019, Stemgent, CA), 2 µM ALK5 inhibitor (SD-208, disclosed in Molecular Pharmacology 2007 72:152-161) and 100 nM Vitamin A (Catalogue# R7632, Sigma, MO) for three days.

Figure 4:
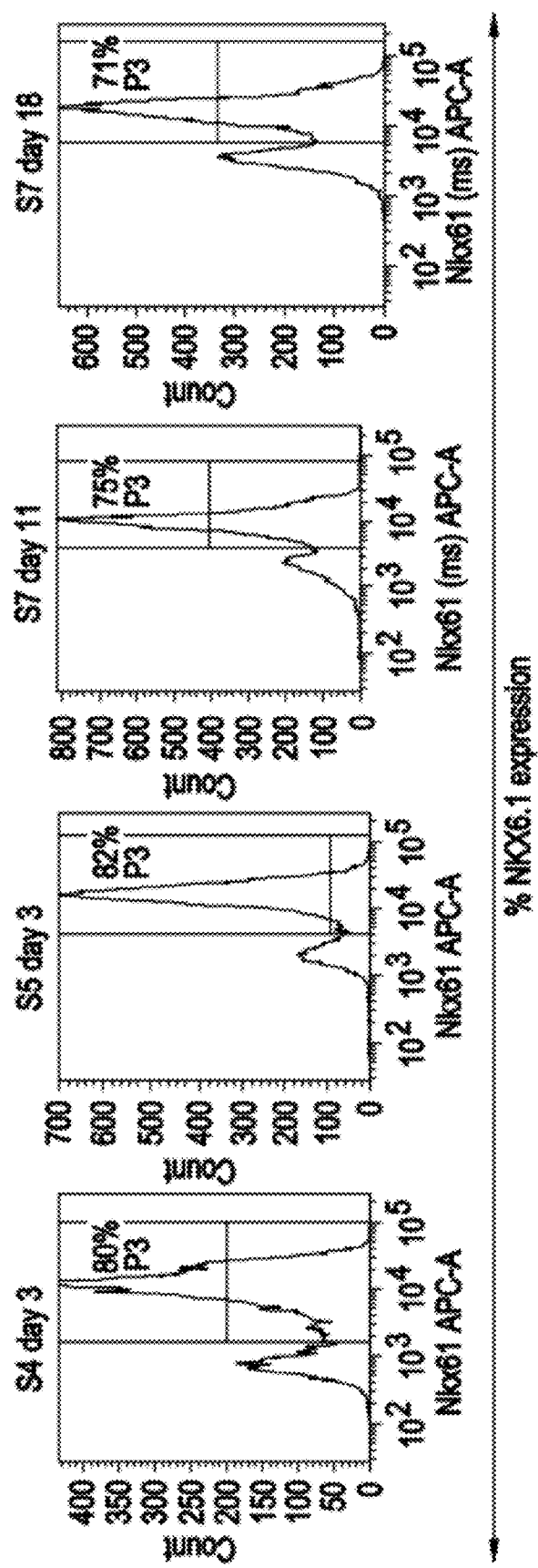
FIG. 4 shows FACS plots for the expression of NKX6.1 in cells at stages IV-VII of the protocol outlined in Example 3.
Figure 5:
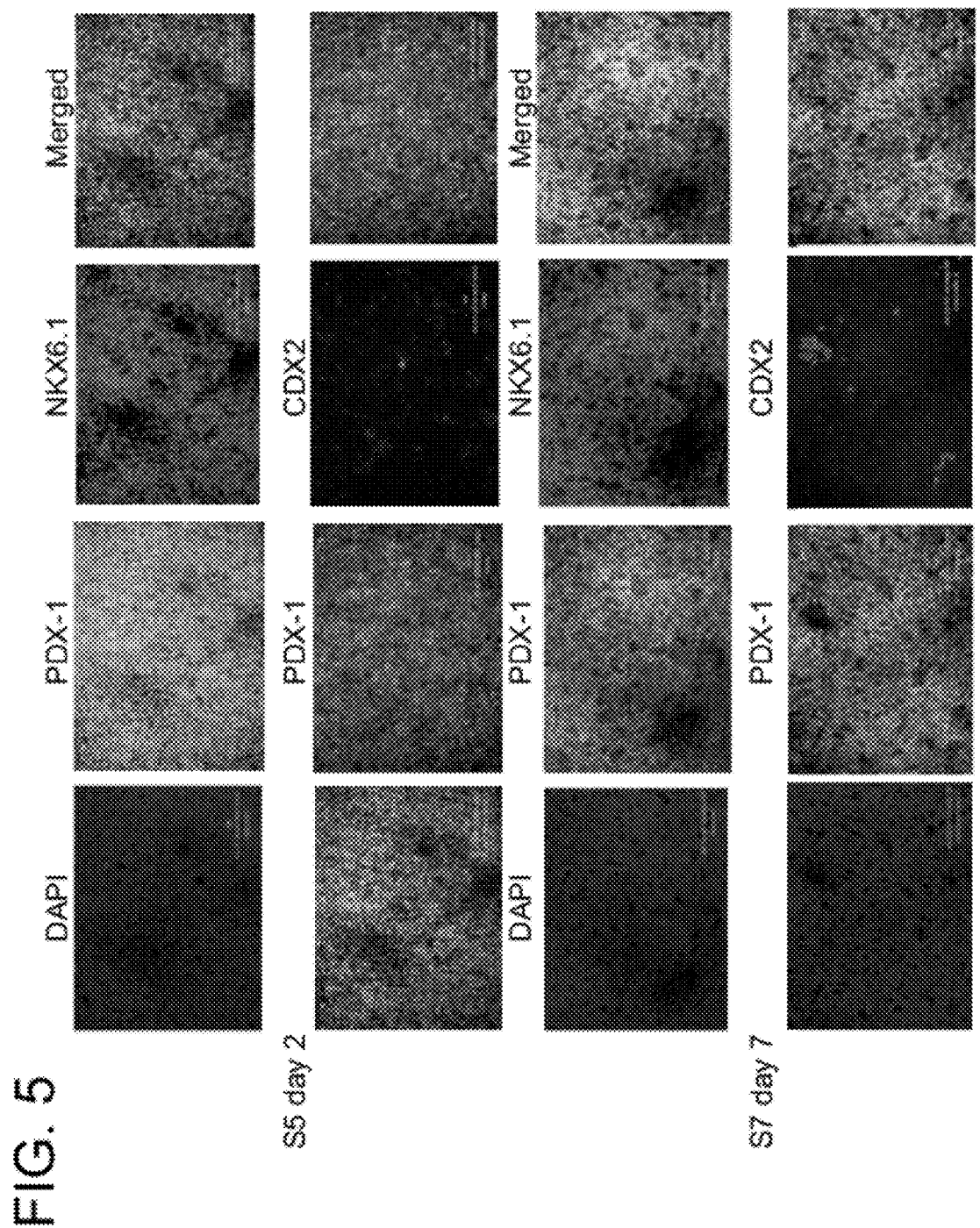
FIG. 5 shoes immunostaining images for PDX1, NKX6.1 and CDX2 in cells at stages V and VII of the protocol outlined in Example 3.

In some of the cultures, stage VII was extended to 18 days. Samples were collected at stages V, VI, and for real-time PCR analysis, immune fluorescence (IF) staining and FACS analysis. For both FACS and immune fluorescence (IF) staining, the NKX6.1 antibody was obtained from University of Iowa hybridoma bank (Catalogue# F55A12), the CDX2 antibody was obtained from Abcam (Catalogue # ab76541, Cambridge, Mass.), and the PDX-1 antibody was purchased from Abcam (Catalogue# ab47267). FIG. 3 highlights the morphology of cultures at various stages of differentiation. Following stage II, the cultures showed homogenous morphology throughout stages III-VI. FIG. 4 depicts the expression of NKX6.1 as measured by FACS for various stages of differentiation. This figure highlights that the protocol disclosed in Example 3, can retain high expression of NKX6.1 through late stages of differentiation. FIG. 5 shows IF staining for PDX1, NKX6.1, and CDX2 expression for stages V and stage VII of the protocol. Greater than 90% of the NKX6.1 positive cells were also PDX1 positive, while less than 10% of the cells stained positive for CDX2.

Publications cited throughout this document are hereby incorporated by reference in their entirety. Although the various aspects of the invention have been illustrated above by reference to examples and preferred embodiments, it will be appreciated that the scope of the invention is defined not by the foregoing description but by the following claims properly construed under principles of patent law.

What is claimed is:

1. A method to derive a population of pancreatic endocrine precursor cells from pluripotent stem cells comprising the steps of:
    a. Culturing a population of pluripotent stem cells;
    b. Differentiating the population of pluripotent stem cells into a population of cells expressing markers characteristic of the definitive endoderm lineage;

c. Differentiating the population of cells expressing markers characteristic of the definitive endoderm lineage into a population of primitive gut tube cells;
d. Differentiating the population of primitive gut tube cells into a population of posterior foregut cells; and
e. Treating the population of posterior foregut cells with a medium supplemented with a CYP26A inhibitor and with no added retinoic acid such that the population of posterior foregut cells differentiates into a population of pancreatic endocrine precursor cells, wherein expression of endocrine precursor markers is increased and wherein the differentiating in steps b., c. and d. comprises treatment in a medium lacking a CPY26A inhibitor.

2. The method of claim 1, wherein the CYP26A inhibitor is used at a concentration from about 1 nM to about 1000 nM.

3. The method of claim 1, wherein the CYP26A inhibitor is used at a concentration from about 10 nM to about 100 nM.

4. The method of claim 1, wherein the CYP26A inhibitor is N-{4-[2-Ethyl-1-(1H-1,2,4-triazol-1-yl)butyl]phenyl}-1,3-benzothiazol-2-amine.

5. The method of claim 1, wherein treatment increases expression of the endocrine precursor markers NGN3, Pax and NeuroD.

6. The method of claim 1, wherein the treatment decreases the expression of CDX2 and albumin.

7. The method of claim 1, wherein the medium supplemented with the CYP26A inhibitor is further supplemented with at least one factor selected from the group consisting of a factor capable of inhibiting BMP, a TGFβ receptor signaling inhibitor, and a PKC activator.

8. The method of claim 7, wherein the factor capable of inhibiting BMP comprises noggin.

9. The method of claim 7, wherein the TGFβ receptor signaling inhibitor comprises an inhibitor of ALK5.

10. The method of claim 9, wherein the inhibitor of ALK5 is ALK5 inhibitor II.

11. The method of claim 7, wherein the PKC activator is selected from the group consisting of (2S,5S)-(E,E)-8-(5-(4-(Trifluoromethyl)phenyl)-2,4-pentadiemoylamino)benzolactam, Indolactam V (ILV), phorbol-12-myristate-13-acetate (PMA), and phorbol-12,13-dibutyrate (PDBu).

12. A method to derive a population of pancreatic endocrine precursor cells from pluripotent stem cells comprising the steps of:
a. Differentiating pluripotent stem cells into a population of cells expressing markers characteristic of the definitive endoderm lineage (Stage I) by the culturing the pluripotent stem cells in a medium supplemented with activin A;
b. Differentiating the population of cells expressing markers characteristic of the definitive endoderm lineage (Stage I) into a population of primitive gut tube cells (Stage II) by culturing the Stage I cells in a medium supplemented with FGF7;
c. Differentiating the population of primitive gut tube cells (Stage II) into a population of posterior foregut cells (Stage III) by culturing the Stage II cells in a medium supplemented with retinoic acid and a P38 inhibitor; and
d. Differentiating the population of posterior foregut cells (Stage III) into a population of Stage IV cells by treating the Stage III cells with a media supplemented with a CPY26A inhibitor and with no added retinoic acid, wherein the treatment increases the expression of endocrine precursor markers and wherein the differentiating in steps a., b. and c. comprises treatment in a medium lacking a CPY26A inhibitor.

13. The method of claim 12, wherein the Stage IV cells are pancreatic endocrine precursors.

14. The method of claim 12, wherein treatment increases expression of the endocrine precursor markers NGN3, Pax and NeuroD.

15. The method of claim 12, wherein treatment decreases the expression of CDX2 and albumin.

16. The method of claim 12, wherein the CYP26A inhibitor is used at a concentration from about 1 nM to about 1000 nM.

17. The method of claim 12, wherein the medium in step c. is further supplemented with at least one or more of FGF7, activin A or a BMP receptor inhibitor.

18. The method of claim 12, wherein the medium supplemented with a CPY26A inhibitor is further supplemented with at least one factor selected from the group consisting of a factor capable of inhibiting BMP, a TGFβ receptor signaling inhibitor, and a PKC activator.

19. The method of claim 18, wherein the factor capable of inhibiting BMP comprises noggin.

20. The method of claim 18, wherein the TGFβ receptor signaling inhibitor comprises an inhibitor of ALK5.

21. The method of claim 20, wherein the inhibitor of ALK5 is ALK5 inhibitor II.

22. The method of claim 18, wherein the PKC activator is selected from the group consisting of (2S,5S)-(E,E)-8-(5-(4-(Trifluoromethyl)phenyl)-2,4-pentadiemoylamino)benzolactam, Indolactam V (ILV), phorbol-12-myristate-13-acetate (PMA), and phorbol-12,13-dibutyrate (PDBu).

* * * * *